United States Patent [19]
von Izstein et al.

[11] Patent Number: 5,360,817
[45] Date of Patent: Nov. 1, 1994

[54] DERIVATIVES AND ANALOGUES OF 2-DEOXY-2,3-DIDEHYDRO-N-ACETYL NEURAMINIC ACID AND THEIR USE AS ANTIVIRAL AGENTS

[75] Inventors: Laurence M. von Izstein, North Fitzray; Wen-Yang Wu, Mount Waverley; Tho V. Phan, Carnegie; Basil Danylec, Box Hill; Betty Jin, Mount Waverley, all of Australia

[73] Assignee: Biota Scientific Management Pty Ltd, Melbourne, Australia

[21] Appl. No.: 946,327

[22] PCT Filed: Apr. 24, 1991

[86] PCT No.: PCT/AU91/00161
§ 371 Date: Nov. 10, 1992
§ 102(e) Date: Nov. 10, 1992

[87] PCT Pub. No.: WO91/16320
PCT Pub. Date: Oct. 31, 1991

[30] Foreign Application Priority Data
Apr. 24, 1990 [AU] Australia ............... PJ9800
Oct. 19, 1990 [AU] Australia ............... PK2896
Feb. 11, 1991 [AU] Australia ............... PK4537

[51] Int. Cl.$^5$ .................. C07D 309/20; A61K 31/35
[52] U.S. Cl. .................. 514/459; 549/13; 549/28; 549/417; 549/419; 549/420; 549/423; 549/424; 514/460
[58] Field of Search ............ 549/424, 13, 28, 417, 549/419, 420, 423; 514/459, 460

[56] References Cited
FOREIGN PATENT DOCUMENTS
1493249 1/1969 Germany .

OTHER PUBLICATIONS
Baumberger et al.—Helvetica Chimica Acta, 1988, 71 pp. 429–445.
Czollner et al.—Helvetica Chimica Acta, 1990, 73 pp. 1338–1357.
Flashner et al.; Arch. Biochem. Biophys., 221(1), 1983, pp. 188–196.
Mack et al., "Synthesis Of 6-Thiosialic Acids And 6-–Thio-N-Acetyl-D-Neuraminic Acid", Tet. Lett., vol. 28, No. 2, 1987, pp. 191–194.
Nakamura et al., "Studies On Sialic Acids, XV. Synthesis of α- and β-α-Glycosides of 3-Deoxy-D-–glycero-D-galacto-2-nonulopyranosonic", Chem. Pharm. Bull. 36(12) 4807–4813 (1988).
Schreiner et al., "Synthesis Of Some 2,3-didehydro-2-deoxysialic Acids Structurally Varied At C-4 And Their Behaviour Towards Sialidase From Vibrio Cholerae", Liebigs Annalen Der Chemie, No. 2, Feb. 1991, pp. 129–134.

Primary Examiner—Johann Richter
Assistant Examiner—Michael B. Hydorn
Attorney, Agent, or Firm—Foley & Lardner

[57] ABSTRACT

Derivatives and analogues of 2-deoxy-2,3-didehydro-N-acetyl neuraminic acid, pharmaceutical formulations thereof, methods for their preparation and their use in the treatment of viral infections, in particular influenza, are described.

10 Claims, No Drawings

DERIVATIVES AND ANALOGUES OF 2-DEOXY-2,3-DIDEHYDRO-N-ACETYL NEURAMINIC ACID AND THEIR USE AS ANTIVIRAL AGENTS

This invention relates to a new class of chemical compounds and to their use in medicine. In particular the invention concerns new 4-substituted-2-deoxy 2,3-didehydro derivatives of α-D-neuraminic acid, methods for their preparation, pharmaceutical formulations thereof and their use as antiviral agents.

Enzymes with the ability to cleave N-acetyl neuraminic acid (NANA), also known as sialic acid, from other sugars are present in many microorganisms. These include bacteria such as *Vibrio cholerae, Clostridium perfringens, Streptococcus pneumoniae,* and *Arthrobacter sialophilus,* and viruses such as influenza virus, parainfluenza virus, mumps virus, Newcastle disease virus, fowl plague virus, and Sendai virus. Most of these viruses are of the orthomyxovirus or paramyxovirus groups, and carry a neuraminidase activity on the surface of the virus particles.

Many of the neuraminidase-possessing organisms are major pathogens of man and/or animals, and some, such as influenza virus, Newcastle disease virus, and fowl plague virus, cause diseases of enormous economic importance.

It has long been thought that inhibitors of neuraminidase activity might: prevent infection by neuraminidase-bearing viruses. Most of the known neuraminidase inhibitors are analogues of neuraminic acid, such as 2-deoxy-2,3-didehydro-N-acetylneuraminic acid (DANA) and its derivatives. See, e.g., Meindl et al., Virology 1974 58 457–63. The most active of these is 2-deoxy-2,3-dehydro-N-trifluoroacetyl-neuraminic acid (FANA), which inhibits multi-cycle replication of influenza and parainfluenza viruses in vitro. See Palese et al., virology 1974 59 490–498.

A number of 2-deoxy-2,3-didehydro-N-acetyl-neuraminic acid derivatives are known in the art. See for example P. Meindl et al., Virology, 58, 457–463 (1974); P. Meindl and H. Tuppy, Mh. Chem, 100 (4), 1295–1306 (1969); M. Flashner et al., Carbohydrate Research, 103, 281–285 (1982); E. Zbiral et al., Liebigs Ann Chem, 159–165 (1989); T. Ogawa and Y. Ito, Tetrahedron Letters, 28 (49), 6221–6224 (1987); T. Goto et al., Tetrahedron letters, 27 (43), 5229–5232 (1986); H. Ogura et al., Chem. Pharm. Bull, 36 (12), 4807–4813 (1988); German Offenlegungschrift P 1439249. Many of these compounds are active in vitro against neuraminidase from *V. cholerae* or Newcastle disease virus as well as that from influenza virus. Neuraminidase in at least some strains of influenza or parainfluenza viruses has also been reported to be inhibited in vitro by 3-aza-2,3,4-trideoxy-4-oxo-D-arabinoctonic acid δ-lactone and O-α-N-acetyl-D-neuraminosyl)2→3)-2-acetamido-2-deoxy-D-glucose. See Zakstel'skaya et al., Vop. Virol. 1972 17 223–28.

Neuraminidase from *Arthrobacter sialophilus* is inhibited in vitro by the glycals 2,3-dehydro-4-epi-N-acetyl-neuraminic acid, 2,3-dehydro-2-deoxy-N-acetylneuraminic acid and 5-acetamido-2,6-anhydro-2,3,5-trideoxy-D-manno-non-2-en-4-ulosonate, and by their methyl esters. See Kumar et al., Carbohydrate Res. 1981 94 123–130; Carbohydrate Res. 1982 103 281–285. The thio analogues 2-α-azido-6-thio-neuraminic acid and 2-deoxy-2,3-didehydro-6-thioneuraminic acid, Mack & Brossmer, Tetrahedron Letters 1987 28 191–194, and the fluorinated analogue N-acetyl-2,3-difluoro-α-D-neuraminic acid, Nakajima et al., Agric. Biol. Chem. 1988 52 1209–1215, were reported to inhibit neuraminidase, although the type of neuraminidase was not identified. Schmid et al., Tetrahedron Letters 1958 29 3643–3646, described the synthesis of 2-deoxy-N-acetyl-α-D-neuraminic acid, but did not report its activity or otherwise against neuraminidase.

None of the known inhibitors of neuraminidase activity in vitro has been shown to possess antiviral activity in vivo, and indeed some, such as FANA, have specifically been shown to be inactive in vivo. Thus the conventional wisdom has accordingly considered that compounds exhibiting in vitro inhibition of viral neuraminidase would not effect an in vivo blockade of virus infection.

Meindl and Tuppy, Hoppe-Seyler's Z. Physiol Chem. 1969 350 1088, described hydrogenation of the olefinic double bond of 2-deoxy-2,3-dehydro-N-acetylneuraminic acid to produce the β-anomer of 2-deoxy-N-acetyl-neuraminic acid. This β-anomer did not inhibit *Vibrio cholerae* neuraminidase.

The most potent in vitro inhibitors of vital neuraminidase have thus been identified as compounds that are based on the neuraminic acid framework, and these are thought by some to be transition-state analogues. Miller et al., Biochem. Biophys. Res. Comm. 1978 83 1479. But while many of the aforementioned neuraminic acid analogues are competitive inhibitors of neuraminidases, to date, none has been reported as showing anti-viral activity in vivo. For example, although a half-planar, unsaturated 6-member ring system has been asserted to be important for inhibitory activity, see Dernick et al. in ANTIVIRAL CHEMOTHERAPY (K. K. Gauri ed.) Academic Press, 1981, at pages 327–336, some compounds characterized by such a system, notably FANA, have been reported not to possess in vivo anti-viral activity. See Palese and Schulman in CHEMOPROPHYLAXIS AND VIRUS INFECTION OF THE UPPER RESPIRATORY TRACT, Vol. 1 (J. S. Oxford ed.) CRC Press, 1977, at pages 189–205.

We have now found novel 4-substituted 2-deoxy-2,3-didehydro derivatives of α-D-neuraminic acid which are active in vivo.

The invention therefore provides in a first aspect compounds of formula (I) or formula (Ia)

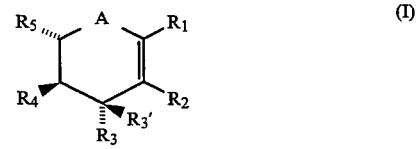

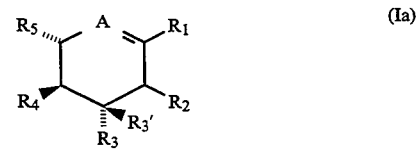

where in general formula (I), A is oxygen, carbon or sulphur, and in general formula (Ia), A is nitrogen or carbon;

$R^1$ denotes COOH, P(O)(OH)$_2$, NO$_2$, SOOH, SO$_3$H, tetrazol, CH$_2$CHO, CHO or CH(CHO)$_2$, $R^2$ denotes H, $OR^6$, F, Cl, Br, CN, $NHR^6$, $SR^6$ or CH2X, wherein X is $NHR^6$, halogen or $OR^6$ and $R^6$ is hydrogen; an acyl group having 1 to 4 carbon atoms; a linear or cyclic alkyl group having 1 to 6 carbon atoms, or a halogen-substituted analogue thereof; an allyl group or an unsubstituted aryl group or an aryl substituted by a halogen, an OH group, an $NO_2$ group, an $NH_2$ group or a COOH group, $R^3$ and $R^{3'}$ are the same or different, and each denotes hydrogen, CN, $NHR^6$, $N_3$, $SR^6$, $=N-OR^6$, $OR^6$, guanidino

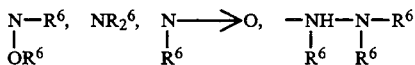
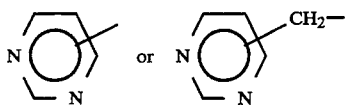

$R^4$ denotes $NHR^6$, $SR^6$, $OR^6$, $COOR^6$, $NO_2$, $C(R^6)_3$, $CH_2COOR^6$, $CH_2NO_2$ or $CH_2NHR^6$, and $R^5$ denotes $CH_2YR^6$, $CHYR^6CH_2YR^6$ or $CHYR^6\text{-}CHYR^6CH_2YR^6$, where Y is O, S, NH or H, and successive Y moieties in an $R^5$ group are the same or different, and pharmaceutically acceptable salts or derivatives thereof.

In both these formulae $R^1$, $R^2$, $R^3$ and $R^{3'}$, $R^4$, $R^5$ and $R^6$ are subject to the provisos that in gernal formula (I), (i) when $R^3$ or $R^{3'}$ is $OR^6$ or hydrogen, and A oxygen or sulphur, then said compound cannot have both
  (a) an $R^2$ that is hydrogen and
  (b) an $R^4$ that is O-acyl or NH-acyl, and
(ii) $R^6$ represents a covalent bond when Y is hydrogen, and that in general formula (Ia),
  (i) when $R^3$ or $R^{3'}$ is $OR^6$ or hydrogen, and A is nitrogen, then said compound cannot have both
  (a) an $R^2$ that is hydrogen, and
  (b) an $R^4$ that is NH-acyl, and
(ii) $R^6$ represents; a covalent bond when Y is hydrogen.

In a preferred embodiment, the compound has general formula (II)

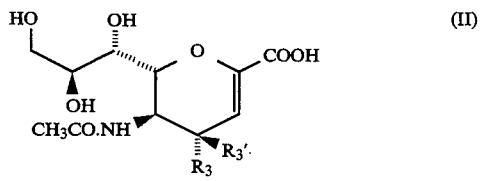

i.e. in general formula (I) above, $R^1$ is COOH, $R^2$ is hydrogen, $R^4$ is acetamido, and $R^5$ is —CHOH.CHOH.CH2OH, and $R^3$ is hydrogen or $R^{3'}$, where $R^{3'}$ denotes $-N_3$, —CN, —CH2NH2, or $-N.R^8.R^9$;

$R^8$ and $R^9$ are the same or different, and each denotes hydrogen, a Linear or cyclic alkyl group of 1 to 6 carbon atoms, an acyl or substituted acyl group of 1 to 6 carbon atoms, —C.(NH).NH2, —CH2.COOH, —CH2CH2—OH or —CH2.CH.($R^{10}$)($R^{11}$), $R^{10}$ and $R^{11}$ may be the same or different, and each denotes oxygen or $R^{12}N=$, and $R^{12}$ denotes hydrogen, —OH, —OCH3, —NH2, or (CH3)2N—.

We have found a particular subclass of compounds formula (I) which are unexpectedly more active than their corresponding 4-hydroxy analogues.

Thus in a particularly preferred aspect the invention provides compounds of formula (Ib)

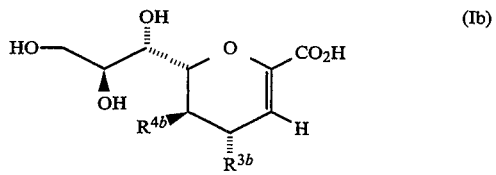

wherein $R^{3b}$ is $(alk)_xNR^{6b}R^{7b}$, CN or $N_3$
where alk is unsubstituted or substituted methylene, x is 0 or 1

$R^{6b}$ is hydrogen, $C_{1\text{-}6}$alkyl (e.g. methyl, ethyl), aryl (e.g. phenyl), aralkyl (e.g. $phenC_{1\text{-}4}$alkyl such as benzyl), amidine, $NR^{7b}R^{8b}$, or an unsaturated or saturated ring containing one or more heteroatoms (such as nitrogen, oxygen or sulphur), $R^{7b}$ is hydrogen, $C_{1\text{-}6}$alkyl (e.g. methyl, ethyl), cr allyl, or $NR^{6b}R^{7b}$ forms an optionally substituted 5 or 6 membered ring optionally containing one or more additional heteroatoms (such as nitrogen, oxygen or sulphur), $R^{8b}$ is hydrogen or $C_{1\text{-}6}$alkyl, and $R^{4b}$ is $NHCOR^{9b}$ where $R^{9b}$ is hydrogen, substituted or unsubstituted $C_{1\text{-}4}$alkyl or aryl, and pharmaceutically acceptable salts of the compounds of formula (Ib) and their pharmaceutically acceptable derivatives.

In the compounds of formula (Ib) the substituents (for example the group $R^6$ in the substituent $R^3$) may themselves bear substituents conventionally associated in the art of pharmaceutical chemistry with such substituents.

Preferably $R^3$ is $NR^6R^7$ in particular $NH_2$ or guanidino.

Preferably $R^4$ is $NHCOR^9$ where $R^9$ is methyl or halogen substituted methyl (e.g. $FCH_2$, $F_2CH-$, $F_3C$).

References herein to preferred definitions of groups in compounds of formula (I) apply mutatis mutandis to the corresponding groups in formulae (Ia), (Ib) and (II).

$C_{1\text{-}4}$alkyl as used herein includes both straight chain (e.g. methyl, ethyl) and branched chain (e.g. isopropyl, t-butyl) alkyl groups.

By pharmaceutically acceptable derivative is meant any pharmaceutically acceptable ester or salt of such ester of the compounds of formula (I) or any other compound which upon administration to the recipient is capable of providing (directly or indirectly) a compound of formula or an antivirally active metabolite or residue thereof.

It will be appreciated by those skilled in the art that the compounds of formula (I) may be modified to provide pharmaceutically acceptable derivatives thereof at any of the functional groups in the compounds. Of particular interest as such derivatives are compounds modified at the C-1 carboxyl function, the C-7 or C-9 hydroxyl functions, or at amino groups. Thus compounds of interest include $C_{1\text{-}4}$alkyl (such as methyl, ethyl or propyl e.g. isopropyl) or aryl (e.g. phenyl, benzoyl) esters of the compounds of formula (I), C-7 or C-9 esters of compounds of formula (I) such as acetyl esters thereof, C-7 or C-9 ethers such as phenyl ethers, benzyl ethers, p-tolyl ethers, and acylated amino derivatives such as formyl, acetamido.

It will be appreciated by those skilled in the art that the pharmaceutically acceptable derivatives of the compounds of formula (I) may be derivatised at more than one position.

Pharmaceutically acceptable salts of the compounds of formula (I) include those derived from pharmaceutically acceptable, inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable, may be useful in the preparation of salts useful as intermediates in obtaining compounds of the invention and their pharmaceutically acceptable acid addition salts.

Salts derived from appropriate bases include alkali metal (e.g. sodium), alkaline earth metal (e.g. magnesium) ammonium and $NR_4^+$ (where R is $C_{1-4}$alkyl) salts.

References hereinafter to a compound of the invention include the compounds of formula (I) and pharmaceutically acceptable salts and derivatives thereof.

Particularly preferred compounds of the invention include:

5-Acetamido-4-amino-2,3,4,5-tetradeoxy-D-glycero-D-galacto-non-2-enopyranosonic acid (also known as 5-(acetylamino)-4-amino-2,6-anhydro-3,4,5-trideoxy-D-glycero-D-galacto-non-2-enoic acid), salts thereof including the sodium salt and 5-Acetamido-4-guanidino-2,3,4,5-tetradeoxy-D-glycero-D-galacto-non-2-enopyranosonic acid (also known as 5-(Acetylamino)-2,6-anhydro-4-guanidino-3,4,5-trideoxy-D-glycero-D-galacto-non-2-enoic acid) and salts thereof, including the ammonium salt.

The compounds of formula (I) possess antiviral activity. In particular these compounds are inhibitors of viral neuraminidase of orthomyxoviruses and paramyxoviruses for example the viral neuraminidase of influenza A and B, parainfluenza, mumps, and Newcastle disease, fowl plague and Sendai virus.

There is thus provided in a further aspect of the invention a compound of formula (I) or a pharmaceutically acceptable salt or derivative thereof for use as an active therapeutic agent, in particular as an antiviral agent, for example in the treatment of orthomyxovirus and paramyxovirus infections.

In a further or alternative aspect there is provided a method for the treatment of a viral infection, for example orthomyxovirus and paramyxovirus infections in a mammal including man, comprising the step of administering to said mammal an effective amount of a compound of formula (I) or a pharmaceutically acceptable salt or derivative thereof.

There is also provided in a further or alternative aspect use of a compound of the invention for the manufacture of a medicament for the treatment of a viral infection.

It will be appreciated by those skilled in the art that reference herein to treatment extends to prophylaxis as well as the treatment of established infections or symptoms.

It will be further appreciated that the amount of a compound of the invention required for use in treatment will vary not only with the particular compound selected but also with the route of administration, the nature of the condition being treated and the age and condition of the patient, and will ultimately be at the discretion of the attendant physician or veterinarian. In general however, a suitable dose will be in the range of from about 0.01 to 750 mg/kg of bodyweight per day preferably in the range of 0.1 to 100 mg/kg/day, most preferably in the range of 0.5 to 25 mg/kg/day.

In particular we have found that the effective doses of the compounds tested are related to their in vitro potency. Thus DANA (which has $IC_{50}$ plaque reduction of 5 μg/ml) has been found to be effective at doses of between i and 10 mg/kg per treatment. The corresponding methyl ester of DANA ($IC_{50}$ 50-100 μg/ml) is effective at proportionally higher dose.

Treatment is preferably commenced before or at the time of infection and continued until virus is no longer present in the respiratory tract. However the compounds are also effective when given post-infection, for example after the appearance of established symptoms.

Suitably treatment is given 1-4 times daily and continued for 3-7, e.g. 5 days post infection depending upon the particular compound used.

The desired dose may be presented in a single dose or as divided doses administered at appropriate intervals, for example as two, three, four or more sub-doses per day.

The compound is conveniently administered in unit dosage from for example containing 10 to 1500 mg, conveniently 20 to 1000 mg, most conveniently 50 to 700 mg of active ingredient per unit dosage form.

While it is possible that, for use in therapy, a compound of the invention may be administered as the raw chemical, it is preferable to present the active ingredient as a pharmaceutical formulation.

The invention thus further provides a pharmaceutical formulation comprising a compound of the formula (I) or formula (Ia), but not subject to the proviso thereto, or a pharmaceutically acceptable salt or derivative thereof together with a pharmaceutically acceptable carrier therefor.

The carrier must be 'acceptable' in the sense of being compatible with the other ingredients of the formulation and not deleterious to the recipient thereof.

The pharmaceutical formulations may be in the form of conventional formulations for the intended mode of administration.

For intranasal administration according to the method of the invention the neuraminidase inhibitors may be administered by any of the methods and formulations employed in the art for intranasal administration.

Thus in general the compounds may be administered in the form of a solution or a suspension or as a dry powder.

Solutions and suspensions will generally be aqueous, for example prepared from water alone (for example sterile or pyrogen-free water), or water and a physiologically acceptable co-solvent (for example ethanol, propylene glycol, and polyethylene glycols such as PEG 400).

Such solutions or suspensions may additionally contain other excipients for example preservatives (such as benzalkonium chloride), solubilising agents/surfactants such as polysorbates (e.g. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose, carboxymethyl cellulose sodium).

Solutions or suspensions are applied directly to the nasal cavity by conventional means, for example with a dropper, pipette or spray. The formulations may be provided in single or multidose foden. In the latter case a means of dose metering is desirably provided. In the case of a dropper or pipette this may be achieved by the patient administering an appropriate, predetermined volume of the solution or suspension. In the case of a spray this may be achieved for example by means of a metering atomising spray pump.

Intranasal administration may also be achieved by means of an aerosol formulation in which the compound is provided in a pressurised pack with a suitable propellant such as a chlorofluorocarbon (CFC), for example dichlorodifluoromethane, trichlorofluoromethane or dichlorotetrafluroroethane, carbon dioxide or other suitable gas. The aerosol may conveniently also contain a surfactant such as lecithin. The dose of drug may be controlled by provision of a metered valve.

Alternatively the compounds may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form, for example in capsules or cartridges of e.g. gelatin or blister packs from which the powder may be administered by means of an inhaler.

In the intranasal formulations the compound will generally have a small particle size, for example of the order of 5 microns or less. Such a particle size may be obtained by means known in the art, for example by micronisation.

When desired the formulations may be adapted to give sustained release of the active ingredient. The compounds of the invention may also be used in combination with other therapeutic agents, for example other antiinfective agents. In particular the compounds of the invention may be employed with other antiviral agents. The invention thus provides in a further aspect a combination comprising a compound of formula (I) or a pharmaceutically acceptable salt or derivative thereof together with another therapeutically active agent, in particular an antiviral agent.

The combinations referred to above may conveniently be presented for use in the form of a pharmaceutical formulation and thus such formulations comprising a combination as defined above together with a pharmaceutically acceptable carrier therefor comprise a further aspect of the invention.

Suitable therapeutic agents for use in such combinations include other anti-infective agents, in particular anti-bacterial and anti-viral agents such as those used to treat respiratory infections. For example, other compounds effective against influenza viruses, such as amantadine, rimantadine and ribavirin, may be included in such combinations.

The individual components of such combinations may be administered either sequentially or simultaneously in separate or combined pharmaceutical formulations.

When the compounds of the invention are used with a second therapeutic agent active against the same virus, the dose of each compound may either be the same as or differ from that employed when each compound is used alone. Appropriate doses will be readily appreciated by those skilled in the art.

The compound of formula (I) and its pharmaceutically acceptable salts and derivatives may be prepared by any method known in the art for the preparation of compounds of analogous structure.

In one such process (A) a compound of formula (III)

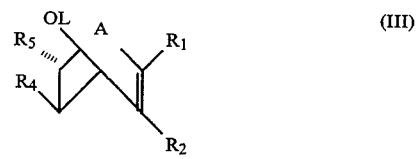

wherein $R^2$ is as defined in formula (I), and L is a leaving group (for example a sulphonic acid residue such as tosyl, mesyl, trifluoromesyl) or a protected derivative thereof is reacted with the appropriate nucleophile, for example azide, cyanide, an appropriate carbanion, or thioacetate.

The compounds of formula (III) may be obtained from the corresponding compounds of formula (IV)

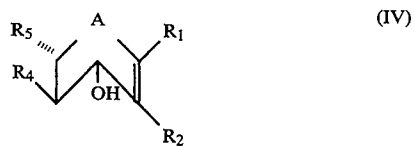

by inversion of the 4—OH group by methods known in the art, for example by reaction with a Lewis acid (such as $BF_3$ etherate) followed by hydrolysis. The compounds of formula (IV) are either known in the art or may be obtained by methods analogous to those for preparing the known compounds.

In a second method (B) the compounds of formula (I) may be prepared from other compounds of formula (I) by interconversion. Thus compounds of formula (I) wherein $R^3$ is $NH_2$ or $CH_2NH_2$ may be prepared by reduction of the corresponding azido or cyano analogues respectively.

Compounds wherein $R^3$ is NH alkyl or guanidino may be prepared by derivatisation of the corresponding compound wherein $R^3$ is $NH_2$.

Compounds of formula I where $R^1$ is COOH may be prepared by hydrolysis of the corresponding ester under either acidic or basic conditions, for example at pH 11-12 (using a base such as sodium or ammonium hydroxide), or at pH 2-3 (using an acid such as sulphuric acid).

As will be appreciated by those skilled in the art, it may be necessary or desirable at any stage in the above described processes to protect one or more sensitive groups in the molecule to prevent undesirable side reactions; the protecting group may be removed at any convenient subsequent stage in the reaction sequence.

The protecting groups used in the preparation of compounds of formula (I) may be used in conventional manner. See for example 'Protective Groups in Organic Chemistry' Ed. J. F. W. McOmie (Plenum Press 1973) or 'Protective Groups in Organic Synthesis' by Theodora W Greene (John Wiley and Sons 1981).

Conventional amino protecting groups may include for example aralkyl groups, such as benzyl, diphenylmethyl or triphenylmethyl groups; and acyl groups such as N-benzyloxycarbonyl or t-butoxycarbonyl. Thus, compounds of general formula (I) wherein one or both of the groups $R^2$ and $R^3$ represent hydrogen may be prepared by deprotection of a corresponding protected compound.

Hydroxy groups may be protected, for example, by aralkyl groups, such as benzyl, diphenylmethyl or triphenylmethyl groups, acyl groups, such as acetyl; silicon protecting groups, such as trimethylsilyl groups; or as tetrahydropyran derivatives.

Removal of any protecting groups present may be achieved by conventional procedures. Thus an aralkyl group, such as benzyl, may be cleaved by hydrogenolysis in the presence of a catalyst (e.g. palladium on charcoal); an acyl group such as N-benzyloxycarbonyl, may be removed by hydrolysis with, for example, hydrogen bromide in acetic acid or by reduction, for example by catalytic hydrogenation; silicon protecting groups may be removed, for example, by treatment with fluoride ion; tetrahydropyran groups may be cleaved by hydrolysis under acidic conditions.

Where it is desired to isolate a compound of the invention as a salt, for example as an acid addition salt, this may be achieved by treating the free base of general formula (I) with an appropriate acid, preferably with an equivalent amount, or with creatinine sulphate in a suitable solvent (e.g. aqueous ethanol).

The present invention is further described by the following examples, which are for illustrative purposes only, and should not be construed as a limitation of the invention.

GENERAL METHODOLOGIES

The following general methods are appliicable to the synthesis of compounds of the invention.

Deacetylation

Treatment of the acetylated material with Amberlite IRA-400 (OH⁻) with stirring, for a period of time, generally 2–3 h, at room temperature results in complete de-O-acetylation. The resin is filtered off and the filtrate concentrated to dryness to afford the desired de-O-acetylation material.

Those skilled in the art would recognise that other standard procedures are available for the complete de-O-acetylation of the same material, such as treatment with sodium methoxide in methanol.

Deesterification

The completely de-O-acetylated material is taken up in aqueous sodium hydroxide and stirred at room temperature for a period of time, generally 2–3 h. The mixture is then adjusted to pH 7.0–7.5 with Dowex 50 w×8 (H+) resin. Filtration followed by freeze-drying of the filtrate affords the desired deesterified material.

Those skilled in the art would readily be able to identify several alternative options for the deesterification of the same material such as acid hydrolysis, alternative base hydrolyses e.g. ammonium hydroxide, potassium hydroxide.

Intermediate compounds referred to in Examples 1 to 15 are identified as follows:

COMPOUND 2

Methyl
5-acetamido-7,8,9-tri-O-acetyl-2,3,5-trideoxy-D-glycero-D-talo-non-2-enopyranosonate
(4-epi-Neu5,7,8,9Ac$_4$2enlMe)

COMPOUND 3

Methyl
5-acetamido-7,8,9-tri-O-acetyl-4-azido-2,3,5-trideoxy-D-glycero-D-galacto-non-2 -enopyranosonate
(4-azido-Neu5,7,8,9Ac$_4$2enlMe)

COMPOUND 5

Methyl
5-acetamido-7,8,9-tri-O-acetyl-4-amino-2,3,4,5-tetradeoxy-D-glycero-D-galacto-non-2-enopyranosonate
(4-amino-Neu5,7,8,9 Ac$_4$2 enlMe)

COMPOUND 8

Methyl
5-acetamido-7,8,9-tri-O-acetyl-4-N,N-diallylamino-2,3,4,5-tetradeoxy-D-glycero-D-galacto-non-2-enopyranosonate (4-N,N-diallylamino-Neu5,7,8,9 Ac$_4$2 enlMe)

COMPOUND 10

Methyl
5-acetamido-7,8,9-tri-O-acetyl-4-N-allylamino-2,3,4,5-tetradeoxy-D-glycero-D-galacto-non-2-enopyranosonate (4-N-allylamino-Neu5,7,8,9 Ac$_4$2 enlMe)

COMPOUND 12

Methyl
5-acetamido-7,8,9-tri-O-acetyl-4-amino-2,3,4,5-tetradeoxy-D-glycero-D-talo-non-2-enopyranosonate
(4-epi-4-aminoNeu5,7,8,9 Ac$_4$2 enlMe)

COMPOUND 13

Methyl
7,8,9-tri-O-acetyl-2,3,5-trideoxy-4',5'-dihydro-2'-methyloxazolo [5,4-d]
D-glycero-D-talo-non-2-enopyranosonate
(4-epi-4,5-oxazaloNeu7,8,9 Ac$_3$2enlMe) COMPOUND 15

Methyl
5-acetamido-7,8,9-tri-O-acetyl-4-azido-2,3,4,5-tetradeoxy-D-glycero-D-talo-non-2-enopyranosonate
(4-epiazidoNeu5,7,8,9 Ac$_4$2 enlMe)

COMPOUND 16

Methyl
5-acetamido-4-azido-2,3,4,5-tetradeoxy-D-glycero-D-talo-non-2-enopyranosonate (4-epi-azidoNeu5 Ac2enlMe)

COMPOUND 18

Methyl
5-acetamido-7,8,9-tri-O-acetyl-4-N-methylamino-2,3,4,5-tetradeoxy-D-glycero-D-galacto-non-2-enopyranosonate (4-N-methylamino-Neu5,7,8,9 Ac$_4$2 enlMe)

COMPOUND 19

Methyl
5-acetamido-4-N-methylamino-2,3,4,5-tetradeoxy-D-glycero-D-galacto-non-2-enopyranosonate
(4-N-methylamino-Neu5Ac2enlMe)

COMPOUND 21

Methyl
5-acetamido-7,8,9-tri-O-acetyl-4-N,N-dimethylamino-2,3,4,5-tetradeoxy-D-glycero-D-galacto-non-2enopyranosonate
(4-N,N-dimethylamino-Neu5,7,8,9Ac$_4$2 enlMe)

COMPOUND 22

Methyl
5-acetamido-4-N,N-dimethylamino-2,3,4,5-tetradeoxy-D-glycero-D-galacto-non-2-enopyranosonate
(4-N,N-dimethylaminoNeu5Ac2enlMe)

COMPOUND 24

Methyl
5-acetamido-7,8,9-tri-O-acetyl-4-N-methoxycarbonyl-methylamino-2,3,4,5-tetradeoxy-D-glycero-D-galacto-non-2-enopyranosonate
(4-N-methoxycarbonylmethylaminoNeu5,7,8,9Ac$_4$-2enlMe)

COMPOUND 25

Methyl
5-acetamido-4-N-methoxycarbonylmethylamino-2,3,4,5-tetradeoxy-D-glycero-D-galacto-non-2-enopyranosonate
(4-N-methoxycarbonylmethylaminoNeu5Ac2enlMe)

COMPOUND 27

Methyl
5-acetamido-7,8,9-tri-O-acetyl-4-N-2'-hydroxyethylamino-2,3,4,5-tetradeoxy-D-glycero-D-galacto-non-2-enopyranosonate
(4-N-2'-hydroxyethylaminoNeu5,7,8,9-Ac$_4$2enlMe)

COMPOUND 28

Methyl
5-acetamido-4-N-2'-hydroxyethylamino-2,3,4,5-tetradeoxy-D-glycero-D-galacto-non-2-enopyranosonate
(4-N-2'-hydroxyethylaminoNeu5,7,8,9Ac$_4$2enlMe)

COMPOUND 29

Methyl
5-acetamido-7,8,9-tri-O-acetyl-4-N-2'-hydroxyethylamino-2,3,4,5-tetradeoxy-D-glycero-D-galacto-non-2-enopyranosonate
(4-N-2'-hydroxyethylaminoNeu5Ac2enlMe)

COMPOUND 30

3-Deoxy-D-glycero-D-galacto-2-nonulopyranosonic acid (KDN)

COMPOUND 31

Methyl
3-Deoxy-D-glycero-D-galacto-2-nonulopyranosonate (KDNlMe)

COMPOUND 32

Methyl
(4,5,7,8,9-penta-O-acetyl-2,3-dideoxy-D-glycero-$\beta$-D-galacto-2-nonulopyranosyl chlorid)onate
(KDN4,5,7,8,9Ac$_5$2$\beta$CllMe)

COMPOUND 33

Methyl
4,5,7,8,9-penta-O-acetyl-2,3-dideoxy-D-glycero-D-galacto-non-2-enopyranosonate
(KDN4,5,7,8,9Ac$_5$2enlMe)

COMPOUND 34

Methyl
2,3-dideoxy-D-glycero-D-galacto-non-2-enopyranosonate (KDN2enlMe)

COMPOUND 36

Hydrazinium
4,5-diamino-2,3,4,5-tetradeoxy-D-glycero-D-galacto-non-2-enopyranosonate (Hydrazinium 4,5-diaminoNeu2en)

COMPOUND 37

4,5-diamino-2,3,4,5-tetradeoxy-D-glycero-D-galacto-non-2-enopyranosonic acid (4,5-diaminoNeu2en)

EXAMPLE 1

The Preparation of Sodium
5-Acetamido-4-azido-2,3,4,5-tetradeoxy-D-glycero-D-galacto-non-2-enopyranosonate (4-Azido-Neu5Ac2en)
(4)

The overall reaction scheme is as follows:

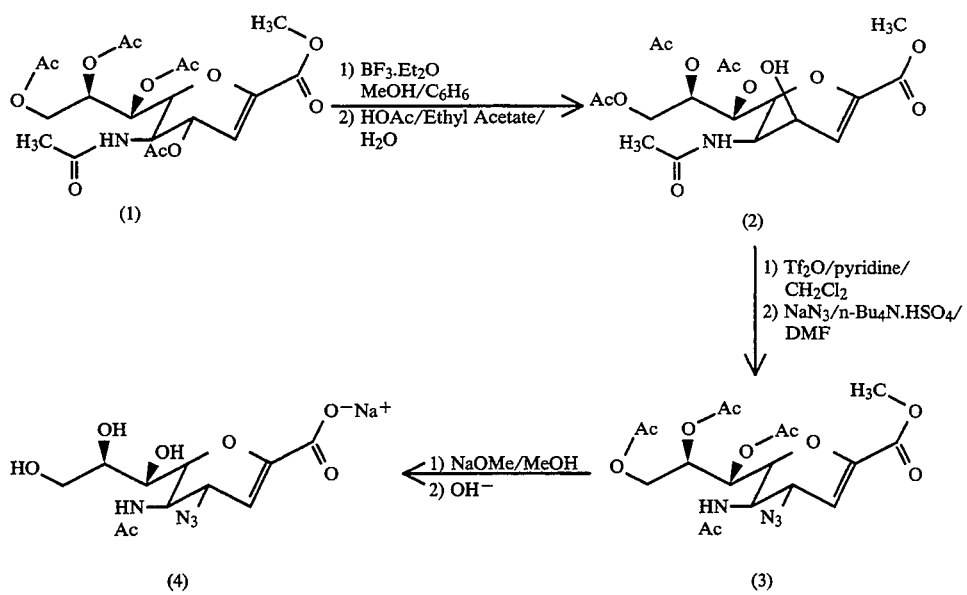

Preparation of (2)

To an agitated solution of methyl 5-acetamido-4,7,8,9-tetra-O-acetyl-2,3,5-trideoxy-D-glycero-D-galacto-non-2-enopyranosonate (1) (1500 mg, 3.17 mmol) in a mixture of benzene (50 ml) and methanol (300 mg) was added dropwise BF$_3$Et$_2$O (12 ml) over thirty minutes under a nitrogen atmosphere at room temperature. The whole mixture was then allowed to stir at room temperature for 16 hours. The solution was diluted with ethyl acetate (250 ml), washed successively with saturated NaHCO$_3$ solution (30 ml×3) and water (20 ml×3), then evaporated to a small volume (about 10 ml), to which was added water (0.5 ml) and acetic acid (0.5 ml). The whole mixture was then stirred at room temperature for two days before being diluted with ethyl acetate (200 ml). The ethyl acetate solution was washed with 5% NaHCO$_3$ solution (30 ml×2) and water (20 ml×3), then evaporated to dryness. The residue was chromatographed (silica gel, ethyl acetate as eluting solvent) to afford pure compound (2) (550 mg, 40%).

$^1$H-nmr (CDCl$_3$) δ (ppm); 1.95, 2.06, 2.08, 2.10, 2.35 (s, 15H, Acetyl CH$_3$×5), 3.80 (s, 3H, COOCH$_3$), 4.1–4.4 (m, 4H, H$_4$, H$_5$, H$_6$, H$_9$), 4.82 (dd, 1H, J$_{9,8}$ 1.8 Hz, J$_{9,9'}$ 12.3 Hz, H$_9$), 5.27 (m, 1H, H$_8$), 5.45 (dd, 1H, J$_{7,8}$ 3.5 Hz, H$_7$), 6.15 (d, 1H, J$_{3,4}$ 5.4 Hz, H$_3$), 6.47 (d, 1H, J$_{NH,5}$ 8.8 Hz, —CONH).

Preparation of (3)

To a stirred solution of compound (2) (800 mg, 1.67 mmol) in anhydrous dichloromethane (10 ml) and dry pyridine (316 mg, 4 mmol) at −30° to −40° C., was added dropwise a solution of trifluoromethane sulphonic anhydride (Tf$_2$O) (556 mg, 2 mmol) in dichloromethane (2 ml) over 15 minutes. The reaction mixture was then stirred at −30° for 5 hours, and concentrated to dryness in vacuo. The residue was then dissolved in dry DMF (5 ml) containing a mixture of sodium azide (650 mg, 10 mmol) and tetrabutylammonium hydrogen sulphate (170 mg, 0.5 mmol). The reaction mixture was stirred at room temperature for 16 hours, and then evaporated to dryness under high vacuum. The residue was partitioned between ethyl acetate (200 ml) and water (50 ml). The organic layer was separated and washed with water (50 ml×2), dried over Na$_2$SO$_4$, evaporated to leave a residue (780 mg), which was subjected to double chromatography (silica gel, the first solvent system was ethyl acetate/acetone: 8/1; the second solvent system was dichloromethane/water: 10/1) to afford a colourless oil (3) (185 mg, 24%).

MS. (FAB) 457 (M$^+$+1) 414 (M$^+$−N$_3$. [α]$^{20}_D$+19.1° (Cl, MeOH).ir.(CHCl$_3$) cm$^{-1}$ 2100 (N-N$_3$). 1748 (carbonyl). $^1$H-nmr (CDCl$_3$) δ (ppm). 2.04, 2.05, 2.06, 2.12, (s, 12H, Acetyl CH$_3$×4). 3.79 (s, 3H, COOCH$_3$), 3.91 (ddd, 1H, J$_{5,NH}$ 8.4 Hz, J$_{5,4}$ 8.8 Hz, J$_{5,6}$ 9.9 Hz, H$_5$), 4.17 (dd, 1H, J$_{9'8}$ 6.8 Hz, J$_{9'9}$, 12.5 Hz, H$_{8'}$), 4.42 (dd, 1H, J$_{4,3}$ 2.9 Hz, J$_{4,5}$ 8.8 Hz, H$_4$), 4.48 (dd, 1H, J$_{6,7}$ 2.3 Hz, J$_{6,5}$ 9.9 Hz, H$_6$ 4.46 (dd, 1H, J$_{9,8}$ 2.7 Hz, J$_{9,9'}$ 12.5 Hz, H$_9$), 5.31 (m, 1H, J$_{8,7}$ 5.2 Hz, J$_{8,9}$ 2.7 Hz, J$_{8,9'}$, 6.8 Hz, H$_8$), 5.45 (dd, 1H, J$_{7,6}$ 2.3 Hz, J$_{7,8}$ 5.2 Hz, H$_7$), 5.96 (d, 1H, J$_{3,4}$ 2.9H, H$_3$), 6.13 (d, 1H, J$_{NH,5}$ 8.4 Hz, —CONH) $^{13}$C-$_{nmr}$ (CDCl$_3$) δ (ppm)

20.7 (CH$_3$—CO—O—), 23.2 (CH$_3$CO—NH), 48.3 (C$_5$), 52.6 (COOCH$_3$), 57.8 (C$_4$), 62.1 (C$_9$), 67.7, 70.9 (C$_7$, C$_8$), 75.9 (C$_6$), 107.6 (C$_3$), 145.1 (C$_2$), 161.5 (C$_1$), 170.2, 170.3, 170.7, (acetyl —C=0×4).

Preparation of (4)

Compound (3) (50 mg, 0.11 mmol) was dissolved in anhydrous methanol (5 ml) containing sodium methoxide (8 mg, 0.15 mmol). The mixture was stirred at room temperature for 2 hours and concentrated to dryness in vacuo. The residue was taken up in water (3 ml), stirred at room temperature for 1.5 hours, ajusted to pH 6–7 with Dowex 50×8 (H+) resin, and then lyophilised to afford the title compound (4) (35 mg, 94%).

i.r. (KBr)cm$^{-1}$ 3400 (br.—OH), 2100 (-N$_3$), 1714 (carbonyl). $^1$H-nmr (D$_2$O) δ (ppm). 2.06 (5, 3H, acetyl CH$_3$), 3.64 (dd, 1H, J$_{9',8}$ 6.3 Hz, J$_{9',9}$ 11.8 Hz, H$_9$'), 3.65 (dd, 1H, J$_{7,6}$ 3.9 Hz, J$_{7,8}$ 6.8 Hz, H$_7$), 3.88 (dd, 1H, J$_{9,8}$ 2.6 Hz, J$_{9,9'}$ 11.8 Hz, H$_9$), 3.94 (m, 1H, J$_{8,7}$ 6.8 Hz, J$_{8,9}$ 2.6 Hz, J$_{8,9'}$ 6.3 Hz, H$_8$), 4.21 (dd, 1H, J$_{5,4}$ 10.4 Hz, J$_{5,6}$ 8.9 Hz, H$_5$), 4.31 (dd, 1H, J$_{4,3}$ 2.2 Hz, J$_{4,5}$ 2.2 Hz, J$_{4,5}$ 10.4 Hz, H$_4$), 4.34 (dd, 1H, J$_{6,5}$ 8.9 Hz, J$_{6,7}$ 3.9 Hz, H$_6$) 5.82 (d, 1H, J$_{3,4}$ 2.2 Hz, H$_3$).

EXAMPLE 2

The Preparation of Sodium 5-Acetamido-4-amino-2,3,4,5-tetradeoxy-D-glycero-D-galacto-non-2-enopyranosonate (4-amino-Neu5Ac2en) (6)

The overall reaction scheme is as follows:

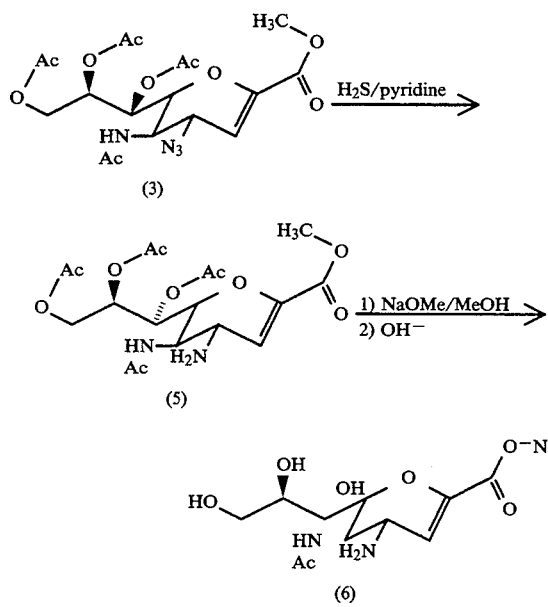

Preparation of (5)

Into a solution of methyl 5-acetamido-7,8,9-tri-O-acetyl-4-azido-2,3,4,5-tetradeoxy-D-glycero-D-galacto-non-2-enopyranosonate (3) prepared as in Example 1, (95 mg, 0,208 mmol) in pyridine (6 ml) was bubbled with H$_2$S for 16 hours at room temperature. The solution was then flushed with nitrogen for 15 minutes, and evaporated to remove pyridine under high vacuum. The residue was chromatographed (silica gel, ethyl acetate/isopropanol/water=5/2/1) to afford a colourless compound (5) (50 mg, 56%).

MS (FAB) 431 (M+ +1), 414 (M+ -NH$_2$), [α]$^{20}_D$+34.5° (Cl, MeOH). i.r. (CHCl$_3$) cm$^{-1}$ 3400 (br.NH$_2$), 1740 (carbonyl). $^1$H-nmr (CDCl$_3$+CD$_3$OD) δ (ppm). 1.96, 2.06, 2.07, 2.10 (s, 12H acetyl CH$_3$×4), 3.81 (S, 3H, —COOCH$_3$), 3.92 (brt, 1H, J$_{5,4}$ & J$_{5,6}$ 10 Hz, H$_5$), 4.17 (dd, 1H, J$_{9',8}$ 7.2 Hz, J$_{9',9}$ 12.3 Hz, H$_{9'}$), 4.22 (br. dd, 2H, J$_{4,5}$ & J$_{6,5}$ 10 Hz, J$_{4,3}$ & J$_{6,7}$ 2.1 Hz, H$_4$ & H$_6$), 4.71 (dd, 1H, J$_{9,8}$ 2.6 Hz, J$_{9,9'}$ 12.3 Hz, H$_9$), 5.31 (m, 1H, J$_{8,7}$ 4.9 Hz, J$_{8,9}$ 2.6 Hz, J$_{8,9'}$ 7.2 Hz, H$_8$), 5.45 (d, 1H, J$_{7,6}$ 2.1 Hz, J$_{7,8}$ 4.9 Hz, H$_7$), 5.97 (d, 1H, J$_{3,4}$ 2.1 Hz, H$_3$).

$^{13}$C-nmr (CDCl$_3$+CD$_3$OD) δ (ppm) 20.2, 20.3 (CH$_3$—CO—O—), 22.3 (CH$_3$—CO—NH), 48.2 (C$_5$), 50.4 (C$_4$), 52.0 (COOCH$_3$), 52.1 (C$_9$), 67.8, 71.2 (C$_7$, C$_8$), 76.5 (C$_6$), 112.5 (C$_3$), 143.5 (C$_2$), 162.0 (C$_1$), 170.2, 170.4, 170.8, 172.2 (acetyl —C=0×4).

Preparation of (6)

Compound (5) (50 mg, 0.116 mmol) was dissolved in anhydrous methanol (5 ml) containing sodium methoxide (12.4 mg, 0.23 mmol). The mixture was stirred at room temperature for 1.5 hours and evaporated to dryness in vacuo at 30° C. The residue was stirred in water (3 ml) at room temperature until TLC (silica gel, ethyl acetate/methanol/0.1N HCl=5/4/1) indicated that hydrolysis was complete. The solution (pH about 10.5) was then gradually adjusted to around pH 7.5 by Dowex 50×8 (H+) resin. As soon as the pH of the solution reached 7.5, the suspension was quickly filtered by a press filter. The filtrate was lyophilised to afford the title compound (6) (30 mg, 83%).

$^1$H-nmr (D$_2$O) δ (ppm). 2.07 (S, 3H, acetyl CH$_3$), 3.59–3.70 m, 2H, H$_7$ & H$_{9'}$), 3.89 (dd, 1H J$_{9,8}$ 2.6 Hz, -J$_{9,9'}$ 11.8 Hz, H$_9$), 3.95 (m, 1H, H$_8$), 3.99 (brd, 1H, J$_{4,5}$ 10.6 Hz, H$_4$), 4.21 (brt, 1H, J$_{5,4}$ & J$_{5,6}$ 10.6 Hz, H$_5$), 4.29 (brd, 1H, J$_{6,5}$ 10.6 Hz, H$_6$), 5.66 (d, 1H J$_{3,4}$ 1.9 Hz, H$_3$).

EXAMPLE 3

The Preparation of Ammonium 5-Acetamido-4-guanidino-2,3,4,5-tetradeoxy-D-glycero-D-galacto-non-2-enopyranosonate (7)

The overall reaction scheme is as follows:

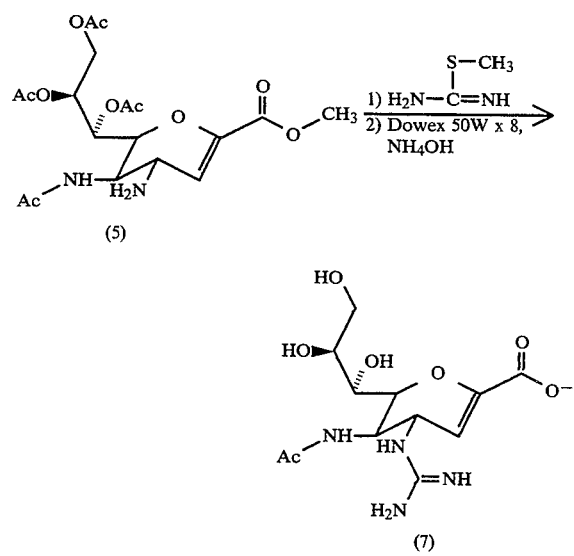

Into a solution of S-methylisourea (546 mg, 3 mmol) in water (15 mL) at ice-bath temperature, methyl-5,7,8,9-tri-O-acetyl-4-amino-2,3,4,5-tetradeoxy-D-glycero-D-galacto-non-2-enopyranosonate (5) prepared as in Example 2 (40 mg, 0.093 mmol) was added. The reaction mixture was stirred at 5° C. for seven days and poured onto a column of Dowex 50 W×8 (H+) resin (35 mL). The column was then washed with cold water (700 mL) and eluted with 1.5 M NH$_4$OH solution. The eluate (120 mL) was concentrated to dryness under high vacuum. The resulting residue was chromatographed (silica gel; solvent system 1: ethyl acetate/isopropanol/-water, 1/5/1; solvent system 2: 75% isopropanol) to provide the title compound (7) (8 mg, 24.5%).

Compound (7) gave a strong, positive Sakaguchi reaction, indicating the presence of a guanidine group. NMR data for compound (7) are given below. $^1$H-nmr (D$_2$O+CD$_3$OD) δ (ppm).

2.06 (s, 2H, acetyl 3.60 (br. d., 1H, $J_{7,8}$ 9.4 Hz, H$_7$), 3.63 (dd, 1H, $J_{9',8}$ 6.2 Hz, $J_{9',9}$ 11.8 Hz, H$_{9'}$), 3.76 (br. d., 1H, $J_{4,5}$ 9.4 Hz, H$_4$), 3.87 (dd, 1H, $J_{9,8}$ 2.67 Hz, $J_{9,9'}$ 11.8 Hz, H$_9$), 3.93 (ddd, 1H, $J_{8,7}$ 9.4 Hz, $J_{8,9}$ 2.6 Hz, $J_{8,9'}$ 6.2 Hz, H$_8$), 4.01 (dd, 1H, $J_{5,4}$ 9.4 Hz, $J_{5,6}$ 10.6 Hz, H$_5$), 4.20 (br. d., 1H $J_{6,5}$ 10.6 Hz, H$_6$), 5.63 (d, 1H, $J_{3,4}$ 2.1 Hz, H$_3$).

EXAMPLE 4

Sodium 5-Acetamido-4-N,N-diallylamino-2,3,4,5-tetradeoxy-D-glycero-D-galacto-non-2-enopyranosonate. (9).

The overall reaction scheme is as follows:

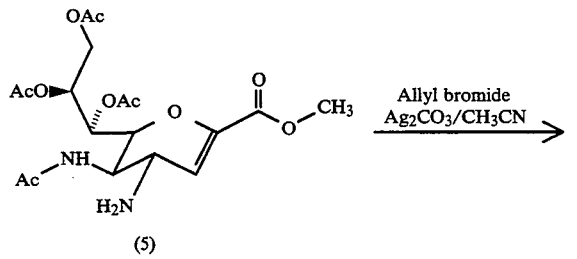

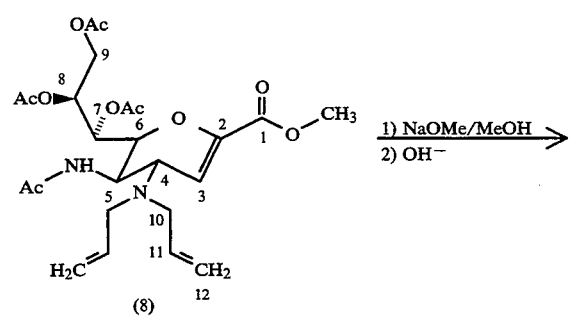

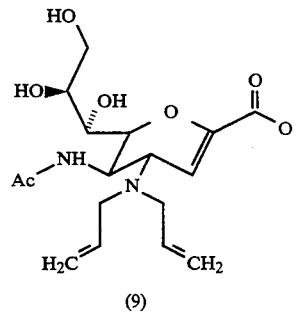

Into a solution of allyl bromide (60 mg, 0.5 mmol) and methyl 5-acetamido-7,8,9-tri-O-acetyl-4-amino-2,3,4,5-tetradeoxy-D-glycero-D-galacto-non-2-enopyranosonate (5) (90 mg, 0.209 mmol) in acetonitrile (5 mL), was added silver carbonate (116 mg, 0.418 mmol). The mixture was stirred and protected from light at room temperature for 16 h. The resulting suspension was filtered, and the filtrate was evaporated to dryness. The residue was subjected to flash-column chromotography silica gel, ethyl acetate containing 10% methanol) to afford methyl 5-acetamido-7,8,9-tri-O-acetyl-4-N,N-diallylamino-2,3,4,5-tetradeoxy-D-glycero-D-galacto-non-2-enopyranosonate (8) (85 mg, 80%).

$^1$H-nmr (CDCl$_3$) δ (ppm) 1.94, 2.05, 2.06, 2.11 (s, 12H, acetyl CH$_3$×4), 2.97 (dd, 2H, $J_{10a,10b}$ & $J_{10'a,10'b}$ 14.3 Hz, $J_{10a,11}$ & $J_{10'a,11'}$ 7.6 Hz, H$_{10a}$ & H$_{10'a}$), 3.24 (dd, 2H, $J_{10b,10a}$ & $J_{10'b,10'a}$ 14.3 Hz, $J_{10b,11}$ & $J_{10',11'}$ 4.9 Hz, H$_{10b}$ & H$_{10'b}$), 3.58 (dd, 1H, $J_{4,3}$ 2.4 Hz, $J_{4,5}$ 9.3 Hz, H$_4$), 3.79 (s, 3H, COOCH$_3$), 4.12–4.26 (m, 3H, H$_6$, H$_{9'}$, H$_5$), 4.70 (dd, 1H, $J_{9,8}$ 2.6 Hz, $J_{9,9'}$ 12.3 Hz, H$_9$), 5.09 (dd, 2H, $J_{12cis,11}$ & $J_{12'cis,11'}$ 10.6 Hz, $J_{12gem}$ & $J_{12'gem}$ ~1.5 Hz, H$_{12cis}$ & H$_{12',cis}$), 5.14 (dd, 2H, $J_{12trans,11}$ & $J_{12'trans,11'}$ 17.7 Hz, $J_{12gem}$ & $J_{12'gem}$ ~1.5 Hz, H$_{12trans}$ & H$_{12'trans}$), 5.27–5.32 (m, 2H, H$_8$ & —CONH—), 5.55 (dd, 1H, $J_{7,6}$ 2.1 Hz, $J_{7,8}$ 4.7 Hz, H$_7$), 5.72 (m, 2H, H$_{11}$ & H$_{11'}$), 6.07 (d, 1H, $J_{3,4}$ 2.4 Hz, H$_3$).

Compound (8) (80 mg, 0.156 mmol) was dissolved in anhydrous methanol (10 mL) containing sodium methoxide (16.2 mg, 0.30 mmol).

The solution was stirred at room temperature for 2 h, then evaporated to dryness. The residue was taken up in water (5 mg), and left at room temperature for 2 h. The resulting solution was neutralized with Dowex 50×8 (H$^+$) and freeze-dried to afford the title compound (9) (49 mg, 80%).

$^1$H-nmr (D$_2$O) δ (ppm) 1.94 (s, 3H, Acetyl CH$_3$), 3.24–3.44 (m, 4H, H$_{10}$×2 & H$_{10'}$×2), 3.48–4.33 (m, 7H, H$_4$, H$_5$, H$_6$, H$_7$, H$_8$, H$_9$ & H$_{9'}$), 5.24–5.29 (m, 4H, H$_{12}$×2 & H$_{12'}$×2), 5.69 (d, 1H, $J_{3,4}$ ~2 Hz, H$_3$), 5.73–5.76 (m, 2H, H$_{11}$ & H$_{11'}$)

EXAMPLE 5

Sodium 5-Acetamido-4-N-allylamino-2,3,4,5-tetra-deoxy-D-glycero-D-galacto-non-2-enopyranosonate (11)

The overall reaction scheme was as follows:

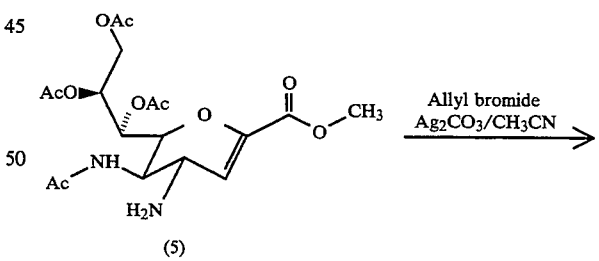

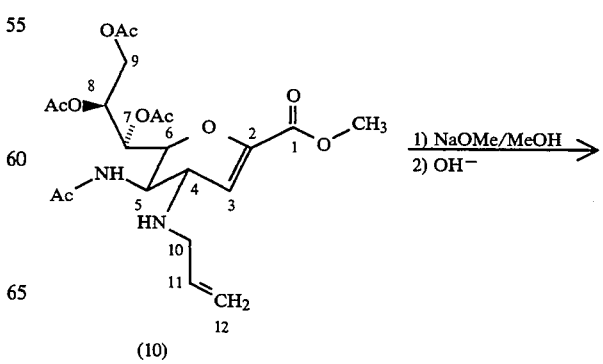

-continued

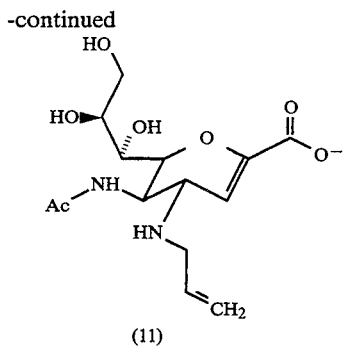

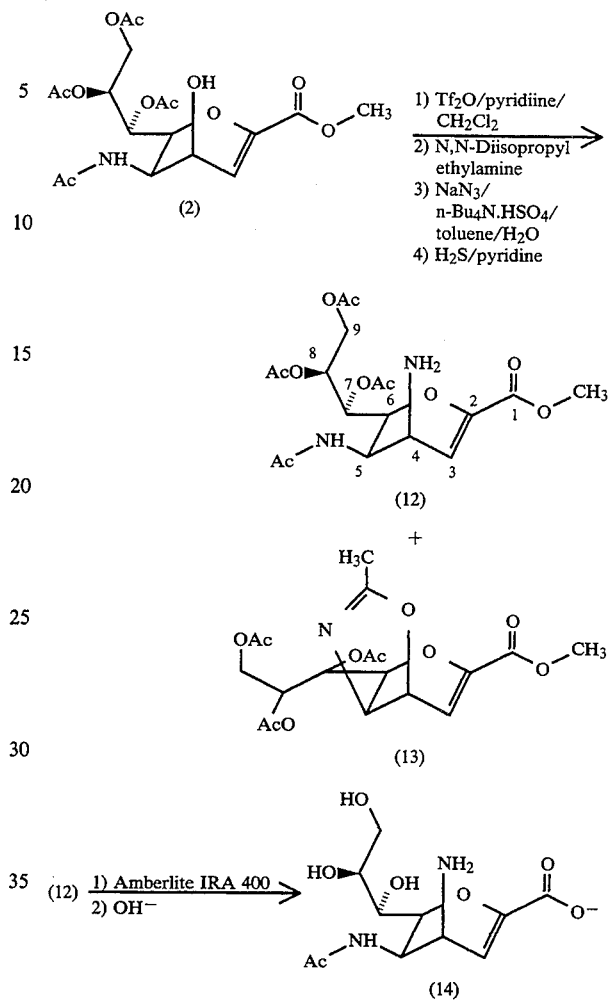

To a solution of allyl bromide (48 mg, 0.40 mmol) and compound (5) (155 mg, 0.36 mmol) in acetonitrile (5 mL) was added silver carbonate (107 mg, 0.38 mmol). The mixture was stirred, whilst protected from light, at room temperature for 16 h. The resulting suspension was filtered off, and the filtrate was evaporated to dryness. The residue was chromatographed on a silica gel column (ethyl acetate/isopropanol/water=5:2:1). Fractions with an Rf value of 0.5 were combined and evaporated to dryness to afford compound (10) (53 mg, 32%). The starting material (5) with an Rf value of 0.3 (61 mg, 39%) and N, N-diallyl derivative (8) with an Rf value of 0.9 (20 mg, 11%) were recovered respectively.

$^1$H-nmr (CDCl$_3$) of compound (10) is shown as follows δ (ppm) 1.96, 2.05, 2.06, 2.11 (s, 12H, Acetyl CH$_3$×4), 3.25 (dd, 1H, $J_{10a,10b}$-14.1 Hz, $J_{10a,11}$ 5.8 Hz, H$_{10a}$), 3.37 (dd, 1H, $J_{10b,10a}$-14.1 Hz, $J_{10b,11}$ 5.9 Hz, H$_{10b}$), 3.43 (dd, 1H, $J_{4,3}$ 3.1 Hz, $J_{4,5}$ 7.5 Hz, H$_4$), 3.79 (s, 3H, COOCH$_3$), 4.09 (ddd, 1H, $J_{5,4}$ 7.5 Hz, $J_{5,NH}$ 1 Hz, $J_{5,6}$ 8.1 Hz, H$_5$), 4.21 (dd, 1H, $J_{9',8}$ 7.1 Hz, $J_{9',9}$-12.2 Hz, H$_9$'), 4.30 (dd, 1H, $J_{6,5}$ 8.1 Hz, $J_{6,7}$ 4.1 Hz, H$_6$), 4.63 (dd, 1H, $J_{9,8}$ 3.2 Hz, $J_{9,9'}$-12.2 Hz, H$_9$), 5.09 (dd, 1H, $J_{12cis,11}$ 10.2 Hz, $J_{12cis,12trans}$-1.3 Hz, H$_{12cis}$), 5.18 (dd, 1H, $J_{12trans,11}$ 17.1 Hz, $J_{12trans,12cis}$-1.3 Hz, H$_{12trans}$), 5.36 (ddd, 1H,$J_{8,7}$ 4.2 Hz, $J_{8,9}$ 3.2 Hz, $J_{8,9'}$ 7.1 Hz, H$_8$), 5.57 (dd, 1H,$J_{7,6}$ 4.1 Hz, $J_{7,8}$ 4.2 Hz, H$_7$), 5.65 (d, 1H, $J_{NH,5}$ 9.1 Hz, —CONH—), 5.83 (dddd,1H, $J_{11,12trans}$ 17.1 Hz, $J_{11,12cis}$ 10.2 Hz, $J_{11,10a}$ 5.8 Hz, $J_{11,10b}$ 5.9 Hz, H$_{11}$), 6.09 (d, 1H, $J_{3,4}$ 3.1 Hz, H$_3$).

Compound (10) (50 mg, 0.11 mmol) was stirred in anhydrous methanol (5 mL) containing sodium methoxide (12 mg, 0.225 mmol) at room temperature for 2 h, then evaporated to dryness. The residue was redissolved in water (5 mL) and allowed to stand at room temperature for 2 h before being neutralized with Dowex 50×8 (H+) resin. The aqueous solution was freeze-dried to afford compound (11) (31 mg, 78%).

$^1$H-nmr (D$_2$O) δ (ppm) 2.02 (s, 3H, CH$_3$ CO), 3.42 (dd, 1H, $J_{10a,10b}$-13.4 Hz, $J_{10a,11}$ 6.6 Hz, H$_{10a}$), 3.52 (dd, , 1H $J_{10b,10a}$-13.4 Hz, $J_{10b,11}$ 6.3 Hz, J$_{10b}$), 3.51–4.27 (m, 7H, H$_4$, H$_5$, H$_6$, H$_7$, H$_8$, H$_9$ & H$_9'$), 5.30 (dd, 1H, $J_{12cis,12trans}$ ~1.5 Hz, $J_{12cis,11}$ 10.3 Hz, H$_{12cis}$), 5.34 (dd, 1H, $J_{12trans,12cis}$~1.5 Hz, $J_{12trans,11}$ 17.7 Hz, H$_{12trans}$), 5.72 (d, 1H, $J_{3,4}$ 2.4 Hz, H$_3$), 5.89 (dddd, $J_{11,10a}$ 6.6 Hz, $J_{11,10b}$ 6.3 Hz, $J_{11,12cis}$ 10.3 Hz, $J_{11,12trans}$ 17.7 Hz, H$_{11}$).

EXAMPLE 6

Sodium 5-Acetamido-4-amino-2,3,4,5-tetra deoxy-D-glycero-D-talo-non-2-enopyranosonate (14)

The overall reaction scheme is as follows:

To a stirred solution of compound (2) (500 mg, 1.04 mmol) in anhydrous dichloromethane (8 mL) containing pyridine (205 mg, 2.6 mmol) at −30°, was added dropwise a solution of trifluoromethanesulphonic anhydride (Tf$_2$O) (367 mg, 1.3 mmol) in dichloromethane (2 mL) over a period of 20 minutes. The reaction mixture was then stirred at −30° for 5 h, and finally evaporated to dryness under reduced pressure. The resulting residue was stirred in dry DMF containing N,N-diisopropylethylamine (194 mg, 1.5 mmol) at room temperature for 16 h. The reaction mixture was concentrated under high vacuum to remove DMF. The residue was then stirred in a two-phase mixture of toluene (5 mL) and water (5 mL) containing tetra-n-butylammonium hydrogen sulphate (950 mg, 2.8 mmol) and sodium azide (137 mg, 2.1 mmol). The mixture was stirred at room temperature for 16 h and then evaporated to dryness. The residue was partitioned between ethyl acetate (50 mL) and water (15 mL), with the organic layer washed successively with water (5 mL×2), and then evaporated to dryness. The residue was taken up in pyridine (5 mL), bubbled with H$_2$S, and then evaporated to dryness. The residue was subjected to flash-column chromatography (silica gel, the first solvent system was ethyl acetate, the second solvent system was ethyl acetate/iso-propanol/H$_2$O: 5/2/1). The ethyl acetate eluate contained compound (13) (260 mg, 53%). The fractions with a positive ninhydrin reaction, collected from the second solvent system, were combined and evaporated to dryness to afford compound (12) (32 mg, 6.5%).

MS (FAB), 431 (M+ +1), 414 (M+ - NH2). $^1$H-nmr (CDCl$_3$+CD$_3$OD) δ (ppm) 1.96, 2.06, 2.08, 2.09 (s, 12H, Acetyl CH$_3$×4), 3.52 (dd, 1H, J$_{4,3}$ 5.5 Hz, J$_{4,5}$ 4.5 Hz, H$_4$), 3.80 (s, 3H, COOCH$_3$), 4.16 (dd, 1H, J$_{6,5}$ 10.2 Hz, J$_{6,7}$ 2.3 Hz, H$_6$), 4.17 (dd, 1H, J$_{9',9}$-12.4 Hz, J$_{9',8}$ 7.3 Hz, H$_{9'}$), 4.23 (dd, 1H, J$_{5,6}$ 10.2 Hz, J$_{5,4}$ 4.5 Hz, H$_5$), 4.73 (dd, 1H, J$_{9,9'}$-12.4 Hz, J$_{9,8}$ 2.7 Hz, H$_9$), 5.34 (ddd, 1H, J$_{8,7}$ 4.7 Hz, J$_{8,9}$ 2.7 Hz, J$_{8,9'}$ 7.3 Hz, H$_8$), 5.45 (dd, 1H, J$_{7,6}$ 2.3 Hz, J$_{7,8}$ 4.7 Hz, H$_7$), 6.12 (d, 1H, J$_{3,4}$ 5.5 Hz, H$_3$).

$^{13}$C-nmr (CDCl$_3$+CD$_3$OD) δ (ppm) 20.7 (CH$_3$C(O)O—), 23.1 (CH$_3$ C(O)N—), 43.8 (C$_5$), 46.2 (C$_4$), 52.4 (COOCH$_3$), 62.3 (C$_9$), 68.3, 71.8 (C$_7$, C$_8$), 73.0(C$_6$), 111.5(C$_3$), 143.8(C$_2$), 162.4 (C$_1$), 170.3 & 170.8 (CH$_3$CO×4).

Compound (12) was stirred in anhydrous methanol (5 mL) containing Amberlite IRA-400 (OH—) resin (100 mg) at room temperature for 3 h. Following filtration, the filtrate was evaporated to dryness. The residue was dissolved in water (5 mL) and adjusted to pH13 with 0.1M NaOH. The aqueous solution was stirred at room temperature for 2 hr and then neutralized with Dowex 50×8 (H+) resin. After filtration, the filtrate was lyophilized to afford compound (14) (16 mg, 70%), which was positive in the ninhydrin reaction.

$^1$H-nmr (D$_2$O) δ (ppm) 2.10 (s, 3H, CH$_3$ CO), 3.67–3.76 (m, 2H, H$_4$ & H$_{9'}$), 3.92 (dd, 1H, J$_{9,8}$ 2.8 Hz, J$_{9,9'}$-11.9 Hz, H$_9$), 3.90–4.02 (m, 2H, H$_7$ & H$_8$), 4.37–4.44 (m, 2H, H$_5$ & H$_6$), 5.81 (d, 1H, J$_{3,4}$ 5.14 Hz, H$_3$).

EXAMPLE 7

Sodium 5-acetamido-4-azido-2,3,4,5-tetradeoxy-D-glycero-D-talo-non-2-enopyranosonate (17).

monium hydrogen sulphate (950 mg, 2.8 mmol) and sodium azide (137 mg, 2.1 mmol). The mixture was stirred at room temperature for 16 h and then was diluted with 0.2M HCl (5 mL). The mixture was stirred at room temperature for 48 h. To this reaction mixture were added ethyl acetate (50 mL) and 2M HCl (1 mL). The organic layer was separated and washed with water (5 mL×3), then evaporated to dryness. The residue was subjected to flash column-chromatography (silica gel, ethyl acetate/hexane=2/1). The fractions with Rf value of 0.32 (ethylacetate/hexane=2/1 as developing solvent) were combined and evaporated to dryness to afford compound (15). (40 mg, 8.4%). The column was then eluted with ethyl acetate/methanol=10/1 to recover the starting material (2) (280 mg,56%). Compound (15) was isolated as a white foam substance.

MS (FAB) 457 (M+ +1), 414 (M+ - N3), i.r. (CHCl$_3$) cm$^{-1}$ 2108 (—N$_3$), 1748 (carbonyl) $^1$H-nmr (CDCl$_3$), δ (ppm)1.97, 2.04, 2.06, 2.07 (s,12H, acetyl CH$_3$×4), 3.82 (s, 3H, COOCH$_3$), 4.12~4.20 (m, 3H,C$_6$, C$_4$ & C$_9$), 4.51 (ddd, 1H, J$_{5,4}$ 4.4 Hz, J$_{5,6}$ 10.7 Hz, J$_5$,NH, 10.1 Hz, H$_5$), 4.69 (dd, 1H, J$_{9,8}$ 2.6 Hz, J$_{9,9'}$12.4 Hz, H$_9$), 5.31 (m, 1H, J$_{8,7}$ 4.9 Hz, J$_{8,9}$ 2.6 Hz, J$_{8,9'}$ 7.0 Hz, H$_8$), 5.45 (dd, 1H, J$_{7,6}$ 2.1 Hz, J$_{7,8}$ 4.9 Hz, H$_7$), 5.68 (d, 1H, J$_{NH,5}$ 10.1 Hz,CONH), 6.15 (d, 1H, J$_{3,4}$ 5.7 Hz, H$_3$)

$^{13}$C-nmr (CDCl$_3$) δ (ppm)
20.7, 20.8, (CH$_3$ CO—O×3), 23.1 (O CH$_3$ CO—NH), 44.8 (C$_5$), 52.6 (COOCH$_3$), 54.8 (C$_4$), 62.1 (C$_9$), 67.6, 71.3 (C$_7$, C$_8$), 73.5 (C$_6$), 104.5 (C$_3$), 146.3 (C$_2$), 161.5 (C$_1$), 169.9, 170.2, 170.5 (acetyl, —C=O×4)

Compound (15) (40 mg, 0.088 mmol) was dissolved in anhydrous methanol (4 mL) containing sodium methoxide (6.4 mg, 0.12 mmol). The mixture was stirred at room temperature for 2 h and concentrated to dryness in vacuo to afford compound (16), which was then

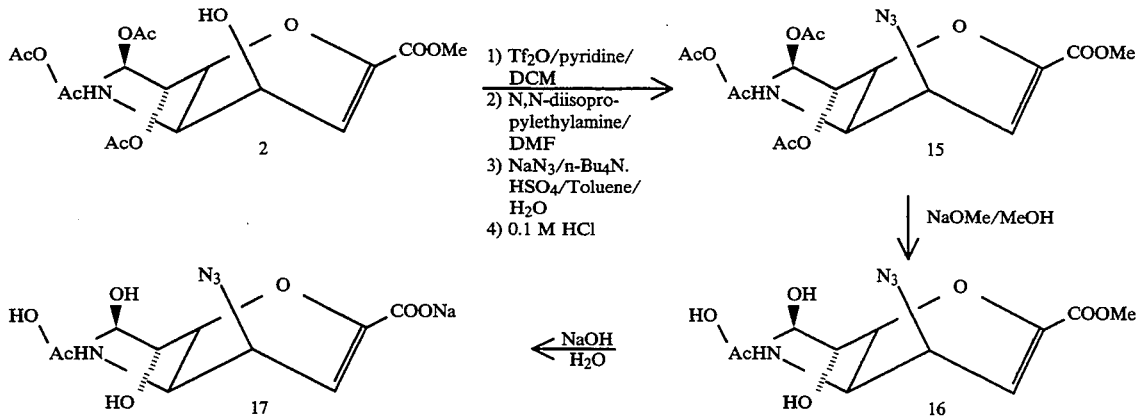

To a stirring solution of compound (2) (500 mg,1.04 mmol) in anhydrous dichloromethane (8 mL) containing pyridine (205 mg, 2.6 mmol) at −30° C., a solution of trifluoromethanesulphonic anhydride (Tf$_2$O) (367 mg, 1.3 mmol) in dichloromethane (2 mL) was added dropwise over a period of 20 minutes. The reaction mixture was then stirrred at 3° C. for 5 h, and finally evaporated to dryness under reduced pressure. The resulting residue was stirred in dry DMF containing N,N-diisopropylethylamine (194 mg, 1.5 mmol) at room temperature for 16 h. The reaction mixture was concentrated under high vacuum to remove DMF. The residue was then stirred in a two-phase mixture of toluene (5 mL) and water (5 mL) containing tetra-n-butylamdissolved in water (3 mL), stirred at room temperature for 2 h, adjusted to pH 6 TM 7 with Dowex 50×8 (H+) resin, and then lyophilised to give the title compound (17) as a yellowish powder (25 mg, 83%). i.r. (KBr) cm$^{-1}$ 3400 (br, —OH), 2108 (—N$_3$), 1714 (carbonyl) $^1$H-nmr (D$_2$O) δ (ppm) 1.97 (s, 3H, acetyl), 3.5~4.4 (m, 7H, H$_4$, H$_5$, H$_6$,H$_7$, H$_8$, H$_9$, & H$_{9'}$), 6.07 (d, J$_{3,4}$ 5.6 Hz, H$_3$)

EXAMPLE 8

Sodium 5-acetamido-4-N-methylamino-2,3,4,5-tetradeoxy-D-glycero-D-galacto-non-2-enopyranosonate (20)

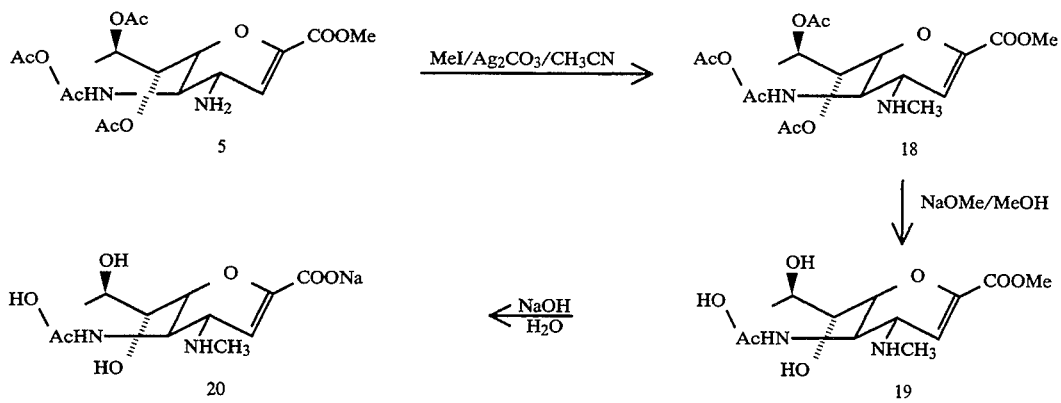

To a solution of methyl iodide (15 mg, 0.10 mmol) and compound (5) (48 mg, 0.11 mmol) in acetonitrile (6 mL) was added silver carbonate (42 mg, 0.15 mmol). The mixture was stirred whilst protected from light, at room temperature for 16 h. The resulting suspension was filtered off, and the filtrate was evaporated to dryness. The residue was subjected to chromatography (silica gel, ethyl acetate/isopropanol/water=5/2/1). Fractions with Rf value of 0.36 were combined and concentrated in vacuum to dryness to afford compound (18) (25 mg, 51%).

MS (FAB) 445 (M+ +1), 414 (M+ - NHCH$_3$)

$^1$H - nmr (CDCl$_3$) δ (ppm) 1.95, 2.05, 2.06, 2.12 (s, 12H, acetyl CH$_3$×4), 2.45 (s, 3H, N—CH$_3$), 3.72 (dd, 1H, J$_{4,3}$ 2.3 Hz, J$_{4,5}$ 9.2 Hz, H$_4$), 3.89 (s, 3H, COOCH$_3$), 4.16 (dd, 1H, J$_{9',8}$ 7.2 Hz, J$_{9',9}$ 12.3 Hz, H$_{9'}$), 4.26 (ddd, 1H, J$_{5,4}$ 9.2 Hz, J$_{5,NH}$ 9.1 Hz, J$_{5,6}$ 9.0 Hz, H$_5$), 4.36 (dd, 1H, J$_{6,5}$ 9.0 Hz, J$_{6,7}$ 2.7 Hz, H$_6$), 4.64 (dd, 1H, J$_{9,8}$ 2.9 Hz, J$_{9,9'}$ 12.3 Hz, H$_9$), 5.34 (m, 1H, J$_{8,7}$ 4.8 Hz, J$_{8,9}$ 2.9 Hz, J$_{8,9'}$ 7.2 Hz, H$_8$), 5.51 (dd, 1H, J$_{7,6}$ 2.7 Hz, J$_{7,8}$ 4.8 Hz), 6.05 (d, 1H, J$_{3,4}$ 2.3 Hz, H$_3$)

Compound (18) (25 mg, 0.056 mmol) was stirred in anhydrous methanol (5 mL) containing sodium methoxide (5.4 mg, 0.1 mmol) at room temperature for 2 h, then evaporated to dryness to give compound (19), which was redissolved in water (5 mL) and allowed to stand at room temperature for 2 h before being neutralized with Dowex 50×8 (H$^+$) resin. The filtrate was lyophilised to afford compound (20) (15 mg, 82%).

$^1$H-nmr (D$_2$O) δ (ppm) 1.94 (s, 3H, CH$_3$ CO), 2.43 (s, 3H, N—CH$_3$), 3.5~4.3 (m, 7H, H$_4$, H$_5$, H$_6$, H$_7$, H$_8$, H$_9$ & H$_{9'}$), 5.65 (d, 1H, J$_{3,4}$ 2 Hz, H$_3$)

EXAMPLE 9

Sodium 5-acetamido-4-N,N-dimethylamino-2,3,4,5-tetradeoxy-D-glycero-D-galacto-non-2-enopyranosonate (23).

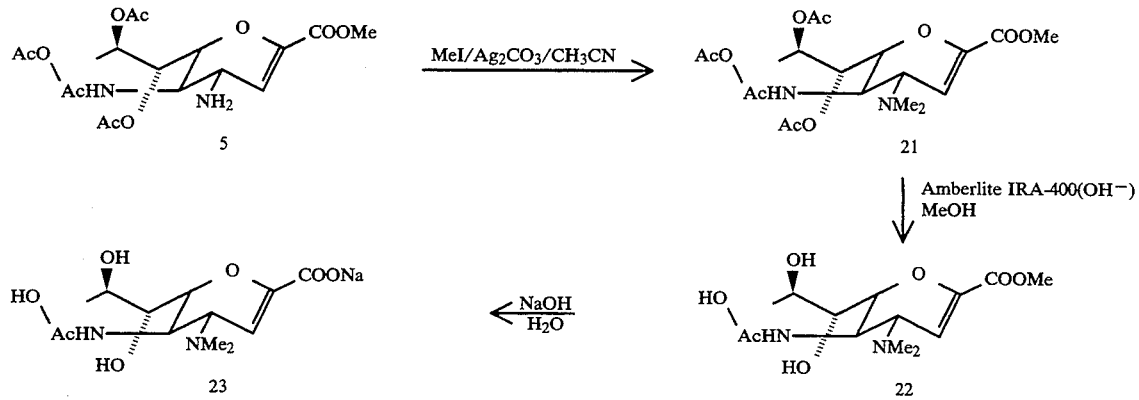

To a solution of methyl iodide (65 mg, 0.46 mmol) and compound (5) (100 mg, 0.23 mmol) in acetonitrile (15 mL) was added silver carbonate (127 mg, 0.46 mmol). The mixture was stirred and protected from light at room temperature for 16 h. The resulting suspension was filtered off and the filtrate was evaporated to dryness. The residue was subjected twice to flash-column chromatography (silica gel, ethyl acetate/isopropanol/water=5/2/1) to afford compound (21) (30 mg, 28%) as a colourless foam.

MS (FAB) 459 (M+ +1) 414 (M+ - N(CH$_3$)$_2$ ) $^1$H-nmr (CDCl$_3$) δ (ppm) 1.98, 2.05, 2.06, 2.12 (s, 12H, acetyl, CH$_3$×4), 2.33 (br s, 6H, N(CH$_3$)$_2$), 3.42 (dd, 1H, J$_{4,3}$ 2.8 Hz, J$_{4,5}$ 8.6 Hz, H$_4$), 3.79 (s, 3H, COOCH$_3$), 4.17 (dd, 1H, J$_{9',8}$ 7.4 Hz, J$_{9',9}$ 12.3 Hz, H$_{9'}$), 4.18 (ddd, 1H, J$_{5,4}$ 8.5 Hz, J$_{5,NH}$ 8.9 Hz, J$_{5,6}$ 9.0 Hz, H$_5$), 4.31 (dd, 1H, J$_{6,5}$ 9.0 Hz, J$_{6,7}$ 2.9 Hz, H$_6$), 4.68 (dd, 1H, J$_{9,8}$ 3.0 Hz, J$_{9,9'}$ 12.3Hz, H$_9$), 5.31 (m, 1H, J$_{8,7}$ 4.4 Hz, J$_{8,9}$ 3.0 Hz, J$_{8,9'}$ 7.4 Hz, H$_8$) 5.51 (dd, 1H, J$_{7,6}$ 2.9 Hz, J$_{7,8}$ 4.4 Hz, H$_7$), 5.79 (d, J$_{NH,5}$ 8.9 Hz, CONH), 6.09 (d, 1H, J$_{3,4}$ 2.8 Hz, H$_3$)

Compound (21) (30 mg, 0.066 mmol) was stirred in anhydrous methanol (4 mL) containing dry Amberlite IRA 400 (OH⁻) resin (90 mg) at room temperature for 3 h, then the resin filtered off. The filtrate and washings were combined and evaporated to dryness to afford compound (22) (20 mg), which was stirred in water (5 mL) at pH 12 at room temperature for 2 h, then was adjusted to pH 7.5 with Dowex 50×8 (H⁺) before filtration. The filtrate was lyophilised to afford compound (23) (15 mg, 66%) as a white powder.

¹H-nmr (D₂O) δ (ppm) 1.97 (s, 3H, acetyl), 2.33 (s, 6H, N(CH₃)₂), 3.50~4.26 (m, 7H, H₄, H₅, H₆, H₇, H₈, H₉ & H₉'), 5.71 (d, $J_{3,4}$ 1.8 Hz, H₃)

EXAMPLE 10

Disodium 5-acetamido-4-N-oxycarbonylmethyl-amino-2,3,4,5-tetradeoxy-D-glycero-D-galacto-non-2-enopyranosonate (26).

1H, $J_{9',8}$ 7.4 Hz, $J_{9',9}$ 12.3 Hz, H₉'), 4.32 (dd, 1H, $J_{6,5}$ 8.1 Hz, $J_{6,7}$ 4.1 Hz, H₆), 4.63 (dd, 1H, $J_{9,8}$ 3.1 Hz, $J_{9,9'}$ 12.3 Hz, H₉), 5.37 (m, 1H, $J_{8,7}$ 4.1 Hz, $J_{8,9}$ 3.1 Hz, $J_{8,9'}$ 7.4 Hz, H₈), 5.56 (t, 1H, $J_{7,6}$ 4.1 Hz, $J_{7,8}$ 4.1 Hz, H₇), 6.03 (d, 1H, $J_{NH,5}$ 8.8 Hz, CONH), 6.04 (d, 1H, $J_{3,4}$ 2.9 Hz, H₃)

Compound (24) (80 mg, 0.159 mmol) was stirred in anhydrous methanol (20 mL) containing sodium methoxide (18 mg, 0.32 mmol) at room temperature for 2 h, then evaporated to dryness to give compound (26), which was redissolved in water (15 mL). The solution was allowed to stand at room temperature for 2 h before being adjusted to pH 7 by Dowex 50×8 (H⁺) resin. The filtrate was freeze-dried to afford compound (25) as a white powder (59 mg, 94.6%).

¹H-nmr (D₂O) δ (ppm) 2.04 (s, 3H, acetyl), 3.58 (AB, 2H, $J_{AB}$ 17.6 Hz, H₁₀×2), 3.50~4.40 (M, 7H, H₄, H₅, H₆, H₇, H₈, H₉ & H₉'), 5.68 (d, 1H, $J_{3,4}$ 2.1 Hz, H₃)

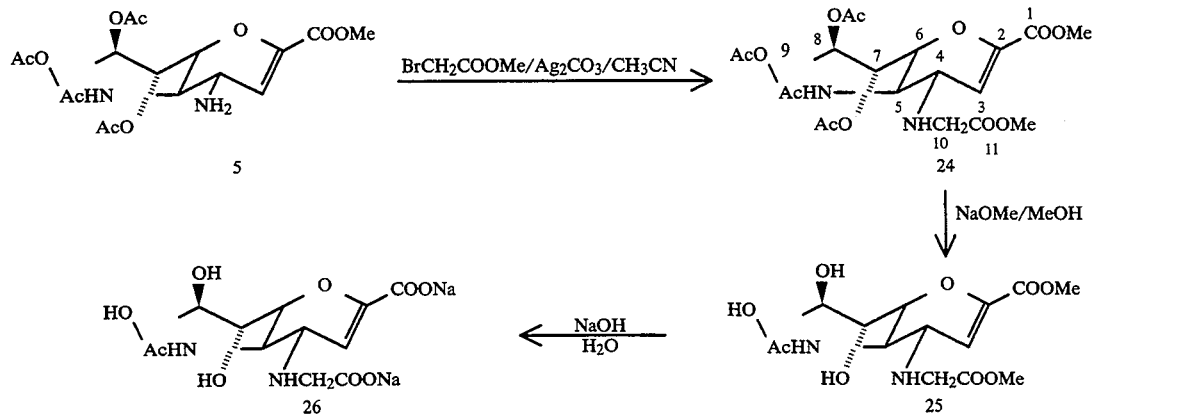

To a solution of methyl α-bromoacetate (36 mg, 0.23 mmol) and compound (5) (100 mg, 0.23 mmol) in acetonitrile (12 mL) was added silver carbonate (64 mg, 0.23 mmol). The mixture was stirred at room temperature for 16 h whilst shielded from light, then filtered. The filtrate was evaporated to dryness. The residue was chromatographed on silica-gel column (ethyl acetate/isopropanol/water=5/2/1). Fractions with Rf value of 0.60 were collected and evaporated to dryness to afford compound (24) (80 mg, 68.5%).

¹H-nmr (CDCl₃) δ (ppm) 1.97, 2.044, 2,047, 2.11 (s, 12H, acetyl CH₃×4), 3.49 (AB, 2H, $J_{AB}$ 17.6 Hz, H₁₀×2), 3.50 (dd, 1H, $J_{4,3}$ 2.9 Hz, $J_{4,5}$ 8.4 Hz, H₄), 3.71 (s, 3H,C₁₁OOMe), 3.79 (s, 3H,C₁ OOMe), 4.09 (ddd, 1H, $J_{5,4}$ 8.4 Hz, $J_{5,NH}$ 8.8 Hz, $J_{5,6}$ 8.1Hz,H₅), 4.17 (dd,

EXAMPLE 11

Sodium 5-acetamido-4-N-2'-hydroxyethylamino-2,3,4,5-tetradeoxy-D-glycero-D-galacto-non-2-enopyranosonate (29)

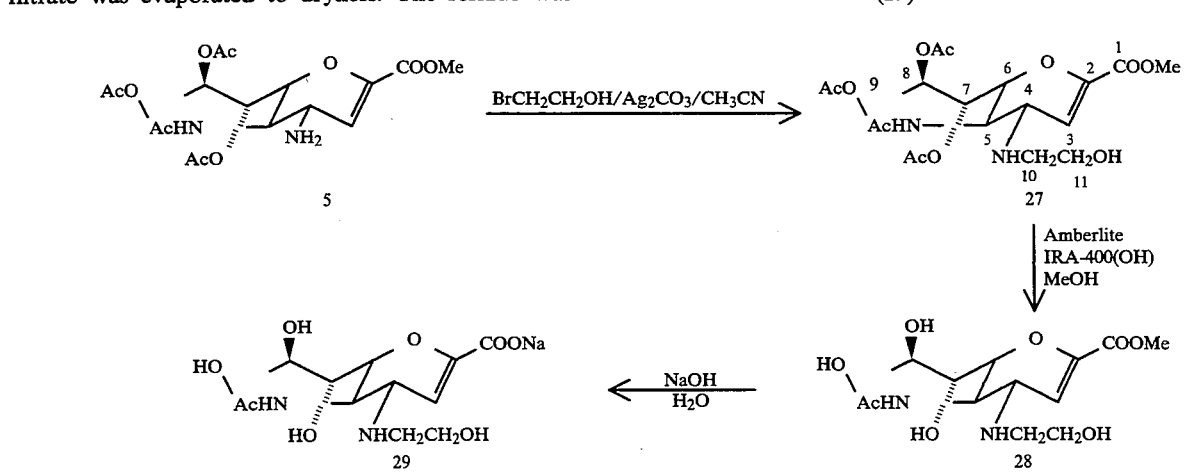

To a solution of bromoethanol (158 mg, 1.26 mmol) and compound (5) (84 mg, 0.195 mmol) in acetonitrile (10 mL) was added silver carbonate (100 mg, 0.36 mmol). The mixture was protected from light and stirred at room temperature for 7 days. Then it was filtered off, the filtrate was evaporated to dryness. The residue was chromatographed on a silica gel column (ethyl acetate/isopropanol/water=5/2/1). Fractions with Rf value of 0.4 were combined and evaporated to dryness to afford compound (27) (40 mL, 40%).

MS (FAB) 475 (M++1), 414 (M+ - NHCH$_2$CH$_2$OH) $^1$H-nmr (CDCl$_3$) δ (ppm) 1.96, 2.05, 2.10 (s, 12H, acetyl CH$_3$×4), 2.29 (br. s, 2H, NH &OH), 2.76 (ABm, 2H, H$_{10}$×2), 3.47 (dd, 1H, J$_{4,3}$ 2.9 Hz, J$_{4,5}$ 7.5 Hz, H$_4$), 3.62 (t, 2H, J$_{11,10}$ 4.9 Hz, H$_{11}$×2), 3.79 (s, 3H, COOCH$_3$), 4.15 (ddd, 1H, J$_{5,4}$ 7.5 Hz, J$_{5,6}$ 8.4 Hz, J$_{5,NH}$ 8.3Hz, H$_5$), 4.19 (dd, 1H, J$_{9',8}$ 7.5 Hz, J$_{9',9}$ 12.3 Hz H$_{9'}$), 4.29 (dd, 1H, J$_{6,5}$ 8.4 Hz, J$_{6,7}$ 3.8 Hz, H$_6$), 4.65 (dd, 1H, J$_{9,8}$ 2.9 Hz, J$_{9,9'}$ 12.3 Hz, H$_9$), 5.36 (m, 1H, J$_{8,7}$ 4 Hz, J$_{8,9}$ 2.9 Hz, J$_{8,9'}$ 7.5 Hz, H$_8$), 5.55 (dd, 1H, J$_{7,6}$ 3.8 Hz, J$_{7,8}$ 4 Hz, H$_7$), 6.08 (d, 1H, J$_{3,4}$ 2.9 Hz, H$_3$), 6.09 (d, 1H, J$_{NH,5}$ 8.3 Hz, CONH)

$^{13}$C-nmr (CDCl$_3$) δ (ppm) 20.6, 20.8, (CH$_3$—CO—O—×3), 23.10 (CH$_3$—Co—NH), 46.5 (C$_5$), 47.2 (C$_{10}$), 52.3 (CH$_3$ COOCH$_3$), 55.6 (C$_4$), 61.1 (C$_{11}$), 62.1 (C$_9$), 68.1, 71.1 (C$_7$, C$_8$), 76.7 (C$_6$), 111.6 (C$_3$), 143.7 (C$_2$), 162.1 (C$_1$), 170.1, 170.3, 170.6, 171.0 (acetyl carbonyl×4)

Compound (27) (40 mg, 0.084 mmol) was stirred in anhydrous methanol (10 mL) containing dry Amberlite IRA-400 (OH$^-$) (120 mg) at room temperature for 4 h, then filtered. The filtrate and washings were combined and evaporated to dryness to give compound (28), which was redissolved in water (10 mL) and adjusted to pH 13 by adding NaOH. The aqueous solution was left at room temperature for 3 h before being adjusted to pH 6 TM 7 with Dowex 50×8 (H+) resin. The solution after filtration was lyophilised to afford compound (29) as a white powder (20 mg 66%).

$^1$H-nmr (D$_2$O) δ (ppm) 1.99 (s, 3H, acetyl), 2.91 (AB, 2H, H$_{10}$×2), 3.53~4.25 (m, 9H, H$_4$, H$_5$, H$_6$, H$_7$, H$_8$, H$_9$, H$_{9'}$, H$_{11}$×2), 5.65 (d, J$_{3,4}$ 2.24 Hz, H$_3$)

EXAMPLE 12

Sodium 2,-3-dideoxy-D-glycero-D-galacto-non-2-enopyranosonate (35)

filtration. The filtrate was evaporated to dryness to give compound (31) (320 mg, 1.13 mmol, 91.5%), which was stirred in acetyl chloride (5 mL) at room temperature for 3 days then evaporated to dryness to afford Compound (32) (539 mg, 1,057 mmol, 93.6%). The residue was dissolved in acetonitrile (20 mL) containing silver nitrate (500 mg, 2.94 mmol) and potassium carbonate (90 mg, 0.65 mmol) protected from light and stirred at room temperature for 16 h, then filtered. The filtrate was evaporated to small volume and partitioned between ethyl acetate (75 mL) and water (15 mL). The organic layer was washed with water (10 mL×3) and evaporated to dryness. The residue was chromatographed on silica gel column (ethyl acetate/hexane=2/1) to afford pure compound (33) (200 mg, 0.423 mmol, 40%).

$^1$H-nmr (CDCl$_3$) δ (ppm) 2.062, 2,070, 2,073, 2.094, 2.096 (s, 15H, acetyl CH$_3$×5), 3.80 (s, 3H, COOCH$_3$), 4.19 (dd, 1H, J$_{9,8}$ 5.9 Hz, J$_{9',9}$ 12.3 Hz, H$_{9'}$), 4.33 (dd, 1H, J$_{6,5}$ 9.4 Hz, J$_{6,7}$ 3.0 Hz, H$_6$), 4.57 (dd, 1H, J$_{9,8}$ 1.9 Hz, J$_{9,9'}$ 12.3 Hz, H$_9$), 5.20 (dd, 1H, J$_{5,4}$ 7.0 Hz, J$_{5,6}$ 9.4 Hz, H$_5$), 5.38 (m, 1H, J$_{8,7}$ 5.1 Hz, J$_{8,9}$ 1.9 Hz, J$_{8,9'}$ 5.9 Hz H$_8$), 5.49 (dd, 1H, J$_{7,6}$ 3.0 Hz, J$_{7,8}$ 5.1 Hz, H$_7$), 5.57 (dd, 1H, J$_{4,3}$ 3.1 Hz, J$_{4,5}$ 7.0 Hz, H$_4$), 5.97 (d, 1H, J$_{3,4}$ 3.1 Hz, H$_3$)

Compound (33) (100 mg, 0,211 mmol) was stirred in anhydrous methanol (10 mL) containing sodium methoxide (24 mg, 0.423 mmol) at room temperature for 3 h, then evaporated to dryness to afford compound (34) (50 mg, 90%), which was redissolved in water (5 mL) and left at room temperature for 3 h before adjusted to pH 7 with Dowex 50×8 (H+) resin. The solution was freeze-dried to give compound (35) (47 mg, 91%).

$^1$H-nmr (D$_2$O) δ (ppm) 3.69 (dd, 1H, J$_{9'8}$ 5.6 Hz, J$_{9'9}$ 12.0 Hz, H$_{9'}$), 3.76 (dd,1H, J$_{5,4}$ 7.8 Hz, J$_{5,6}$ 10.5 Hz H$_5$), 3.87~3.99 (m, 3H, H$_7$, H$_8$, H$_9$), 4.13 (d, 1H, J$_{6,5}$ 10.5 Hz, H$_6$), 4.40 (dd, 1H, J$_{4,3}$ 2.3 Hz, J$_{4,5}$ 7.8 Hz, H$_4$), 5.67 (d, 1H, J$_{3,4}$ 2.3 Hz H$_3$)

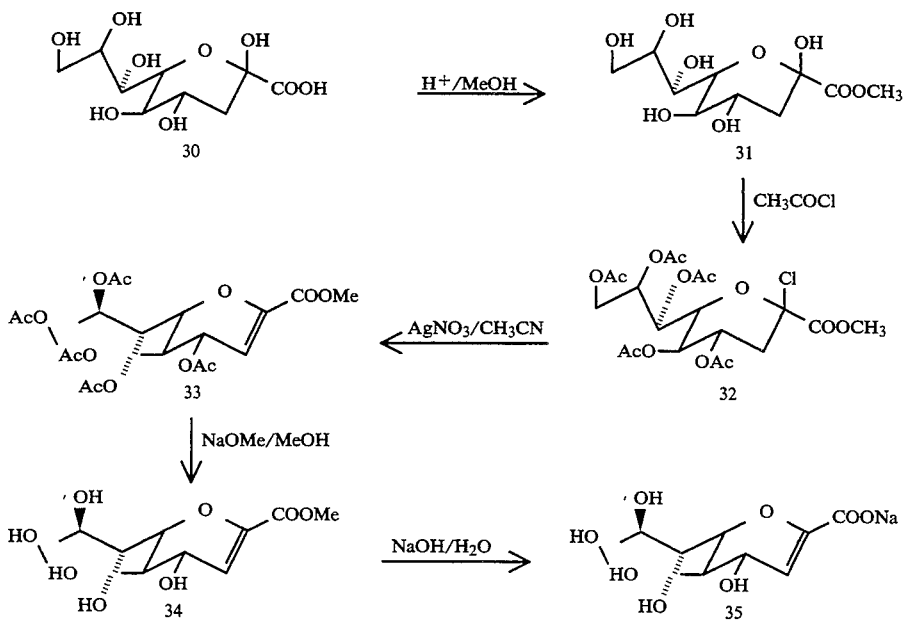

Compound (30) (332 mg, 1.24 mmol) was stirred in anhydrous methanol (40 mL) containing Dowex 50×8 (H+) resin (50 mg) at room temperature for 16 h before

EXAMPLE 13

Sodium 4,5-Diamino-2,3,4,5-tetradeoxy-D-glycero-D-galacto-non-2-enopyranosonate (38)

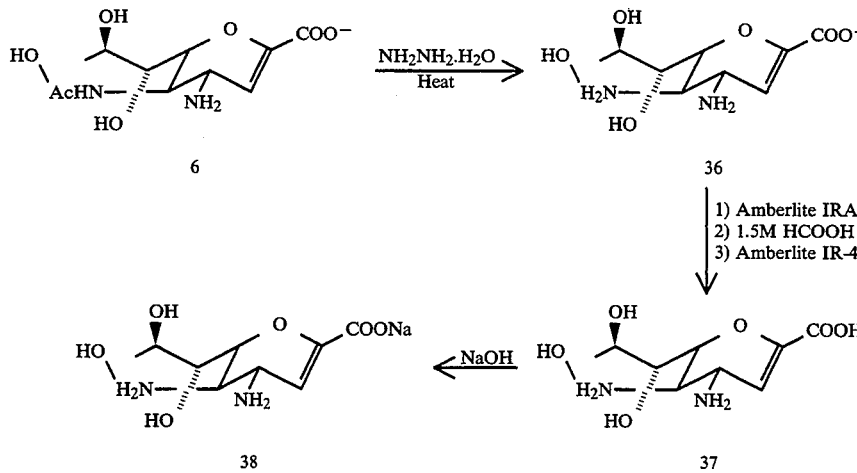

A solution of compound (6) (125 mg, 0.40 mmol) in hydrazine hydrate (5 mL) under argon was heated at 85° C. for 3 days, and the resulting mixture was vacuum evaporated to dryness. The residue was dissolved in water (15 mL) and passed through a column of Amberlite IRA-400 (HCOO−), then eluted with 1.5M HCOOH. The eluate (200 mL) was evaporated to dryness. The residue was chromatographed on silica gel deactivated with 10% water (developing solvent: isopropanol/water=4/1). The fractions with $R_f$ value of 0.1 were combined and evaporated to dryness, then freeze-dried. The residue, compound (36), was dissolved in water (10 mL), passed through a small column of Amberlite IR-4B (OH−)(10 mL). The effluent was evaporated to dryness to give compound (37), MS (FAB) of which was 249 (M+ +1). Compound (37) was dissolved in water and adjusted to pH 7.5 with 0.1M NaOH, then freeze-dried to afford compound (38) (20 mg, 20%) as a white powder.

$^1$H-nmr (D$_2$O) δ (ppm) 3.01 (dd, 1H, J$_{5,4}$ 9.7 Hz, J$_{5,6}$ 10.2 Hz, H$_5$), 3,58 (m, 2H, H$_9$, & H$_7$), 3.80 TM 3.89 (m, 3H, H$_4$, H$_8$, & H$_9$), 4.06 (d, 1H, J$_{6,5}$ 10.2 Hz, H$_6$), 5.54 (d, 1H, J$_{3,4}$ 2.4 Hz, H$_3$)

EXAMPLE 14

Methyl 5-acetamido-2,3,5-trideoxy-9-(p-toluenesulphonyl)-D-glycero-D-galacto-non-2-enopyranosonate (39).

A solution made up of methyl 5-acetamido-2,3,5-trideoxy-D-glycero-D-galacto-non-2-enopyranosonate (1000 mg., 3.16 mmol) in dry pyridine (85 mL) was cooled in an ice-bath. p-Toluenesulphonyl chloride (660 mg., 3.46 mmol) was added and the pale yellow homogeneous solution left to stir overnight at 4° C.

Further p-toluenesulphonyl chloride (220 mg., 1.15 mmol) was added and the solution left to stir for an additional 4 h at room temperature.

Workup was first by addition of water (1 mL) followed by rotary evaporation to afford a viscous yellow oil which was flash chromatographed (SiO$_2$, EtOAc/i-PrOH/H$_2$O, 6/2/1, v/v/v) to give as the major product 1.19 g. (80% yield) of compound (39).

i.r (KBr): υ$_{max}$ (cm$^{-1}$) 2964 (OH), 1730 (CO$_2$CH$_3$), 1656 (NHAc), 1358, 1174 (SO$_2$), 810, 662, 550 (Ar) MS (FAB); 460 (M+H+) 1H nmr (300 MHz, CD$_3$OD/TMS); δ (ppm)=2.03 (s, 3H, NHAc), 2.45 (s, 3H, ARCH$_3$), 3.49 (d, 1H, J$_{6,7}$1.70, H$_6$), 3.76 (s, 3H, CO2CH$_3$), 3.91 (dd, 1H, J$_{5,6}$ 10.80, H$_5$), 3.98–4.13 (m, 3H, HS, H$_9$ and H$_9$), 4.28 (dd, 1H, J$_{7,8}$ 9.55, H$_7$), 4.39 (dd, 1H, J$_4$ 58.64, H$_4$), 5.92 (d, 1H, J$_{3,4}$ 2.49, H$_3$), 7.74 (d, 2H, ArH), 7.79 (d, 2H, ArH)

EXAMPLE 15

Methyl 5-acetamido-9-azido-2,3,5,9-tetradeoxy-D-glycero-D-galacto-non-2-enopyranosonate (40)

Methyl 5-acetamido-2,3,5-trideoxy-9-(p-toluenesulphonyl)-D-glycero-D-galacto-non-2-enopyranosonate (39) (600 mg., 1.27 mmol) and lithium azide (186 mg., 3.80 mmol) were dissolved in dry DMF (20 mL) and the yellow homogenous solution heated to 80° C. After 2 h, further lithium azide (186 mg., 3.80 mmol) was added and the solution left at 80° C. overnight. The solvent was removed by rotary evaporation and the remaining dark brown oil dissolved in pyridine (2 mL) and flash chromatographed (SiO$_2$, 5/2/1 EtOAc/i-PrOH/H$_2$0). The major product was compound (40) (370 mg., 88% yield) obtained as a white foam.

i.r.(KBr):υ$_{max}$(cm$^{-1}$) 3428 (s,OH), 2104 (s, N3), 1730 (s, CO$_2$CH$_3$), 1656 (s, NHAc) MS (FAB): 331 (M+H+) 1H nmr (300 MHz, D$_2$O): δ (ppm) =1.94 (s, 3H, NHAc), 3.37 (dd, 1H, H$_9$), 3.48–3.57 (m, 2H, J$_{8,9'}$ 5.77, H$_8$ and J$_{9,9'}$ 13.16, H$_9$), 3.66 (s, 3H, CO2CH$_3$), 3.91–3.98 (m, 2H, H$_5$ and H$_6$), 4.15 (d, 1H, J$_{7,8}$ 10.86, H$_7$), 4.38 (dd, 1H, J$_{4,5}$ 8.88, H$_4$), 5.91 (d, 1H, J$_{3,4}$ 2.44, H$_3$)

EXAMPLE 16

Methyl 5,9-diacetamido-2,3,5,9-tetradeoxy-glycero-D-galacto-non-2-enopyranosonate (41).

Thiolacetic acid (130 mL, 1.82 mmol) was added to methyl 5-acetamido-9-azido-2,3,5,9-tetradeoxy-D-glycero-D-galacto-non-2-enopyranosonate (70 mg.,0.21 mmol) to give a pale yellow solution that was left to stir overnight at room temperature.

Excess thiolacetic acid was then evaporated off under low pressure and the remaining solid repeatedly treated with water followed by evaporation (3×3 mL). The remaining solid was dissolved in methanol (4 mL), filtered and the filtrate applied to a preparative tlc plate (SiO$_2$, 20 cm.×cm.×2 mm. eluted with 5/2/1 EtOAc-/i-PrOH/H$_2$O). The band with R$_f$=0.47 was worked up to give 51 mg. (70% yield) of compound (41) as a white powder.

i.r. (KBr): $v_{max}$ (cm$^{-1}$) 3400 (s, OH), 1728 (s,CO2CH$_3$), 1656 (s, NHAc) MS (FAB): 347 (M+H$^+$) $^1$H nmr (300 MHz, D$_2$O): δ (ppm) =1.96 (s, 3H, NHAc), 2.00 (s, 3H, NHAc), 3.23 (dd, 1H, H$_9$'), 3.48 (d, 1H, H$_6$), 3.56 (dd, 1H, J$_{9,9'}$ 14.17, H$_9$), 3.75 (s, 3H, CO2CH$_3$), 3,89 (m, 1H, J$_{8,9}$ 2.90, J$_{8,9'}$ 7.40, H$_8$), 4.02 (dd, 1H, J$_{5,6}$ 9.10, H$_5$), 4.22 (d, 1H, J$_{7,8}$ 10.85, H$_7$), 4.45 (dd, 1H, J$_{4,5}$ 8.94, H$_4$), 5.61 (d, 1H, J$_{3,4}$ 2.47, H$_3$);

EXAMPLE 17

5,9-diacetamido-2,3,5,9-tetradeoxy-D-glycero-D-galacto-non-2-enopyranosonic acid (42).

The preparation of compound (42) from compound (39) is summarized below:

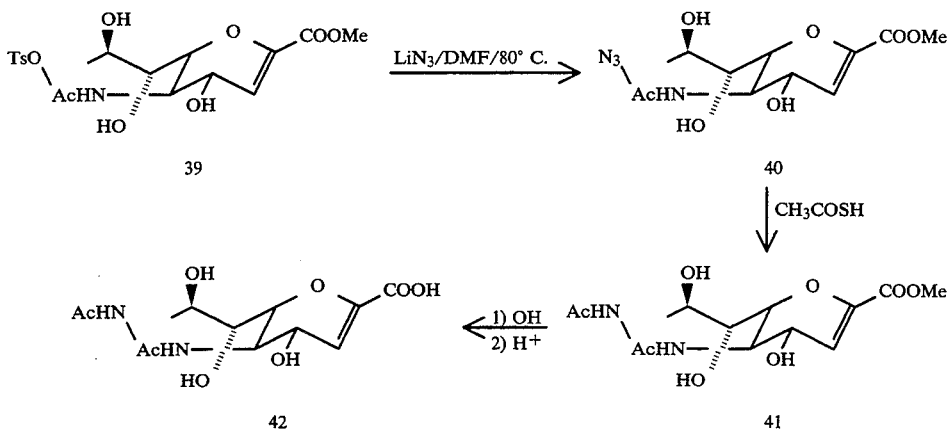

A solution of methyl 5,9-diacetamido-2,3,5,9-tetradeoxy-D-glycero-D-galacto-non-2-enopyranosonate (41) (46 mg., 0.13 mmol) dissolved in 0.1M aq. sodium hydroxide (5 was stirred at room temperature for 2.5 h. The solution was then adjusted to pH 5 with Dowex 50 W-X8 (H$^+$), the resin filtered off and the filtrate lyophilized to give 40 mg. (91% yield) of compound (42) as a white powder.

i.r. (KBr): $v_{max}$ (cm$^{-1}$) 3376 (s, OH), 1652 (s, NHAc) MS (FAB): 333 (M+H$^+$) 1H nmr (300 MHz, D$_2$O): δ (ppm)=1.89 (s, 3H, NHAc), 1.93 (s, 3H, NHAc), 3.15 (dd, 1H, H$_9$'), 3.40 (d, 1H, H$_6$), 3.48 (dd, 1H, J$_{9,9'}$ 14.18, H$_9$), 3.82 (m, 1H, J$_{8,9}$ 3.01, J$_{8,9'}$ 7.43, H$_8$), 3.94 (dd, 1H, J$_{5,6}$ 10.42, H$_5$), 4.13 (d, 1H, J$_{7,8}$ 10.91, H$_7$), 4.36 (dd, 1H, J$_{4,5}$ 8.80, H$_4$), 5.81 (d, 1H, J$_{3,4}$ 2.41, H$_3$)

EXAMPLE 18

Methyl 5-acetamido-9-cyano-2,3,5,9-tetradeoxy-D-glycero-D-galacto-non-2-enopyranosonate (43)

A solution of methyl 5-acetamido-2,3,5-trideoxy-9-(p-toluenesulphonyl)-D-glycero-D-galacto-non-2-enopyranosonate (39) (80 mg., 0.17 mmol), tert-butylammonium cyanide (2 mg) and sodium cyanide (12 mg., 0.25 mmol) in dry DMSO (1.25 mL) was stirred at room temperature for 5 days.

Workup by preparative thin layer chromatography (SiO$_2$, 20 cm.×20 cm.×2 mm. eluted with EtOAc/i-PrOH/H$_2$O, 5/2/1) gave as the major component 30 mg. (61% yield) of compound (43) as a cream coloured powder.

(R$_f$=0.74).

i.r.(KBR): $v_{max}$ (cm$^{-1}$) 3440 (s, OH), 2256 (w, CN), 1726 (s, CO$_2$CH$_3$), 1638 (s, NHAc) MS (FAB): 315 (M+H$^+$) 1H nmr (300 mHz, D$_2$O): δ (ppm)=1.92 (s, 3H, NHAc), 2.75 (dd, 1H, H$_9$'), 2.93 (dd, 1H, J$_{9,9'}$ 17.22, H$_9$), 3.55 (dd, 1H, J$_{6,7}$ 1.17, H$_6$), 3.67 (s, 3H, CO$_2$CH$_3$), 4.02 (dd, 1H, J$_{5,6}$ 9.05, H$_5$), 4.13–4.19 (m, 1H, J$_{8,9}$ 3.91, J$_{8,9'}$6.56, H$_8$), 4.16 (dd, 1H, J$_{7,8}$ 10.90, H$_7$), 4.37 (dd, 1H, J$_{4,5}$ 8.95, H$_4$), 5.90 (d, 1H, J$_{3,4}$ 2.42, H$_3$)

EXAMPLE 19

5-Acetamido-9-cyano-2,3,5,9-tetradeoxy-D-glycero-D-galacto-non-2-enopyranosonic acid (44).

The methodology used to prepare 5-acetamido-9-cyano-2,3,5,9-tetradeoxy-D-glycero-D-galacto-non-2-enopyranosonic acid (44) is summarised below:

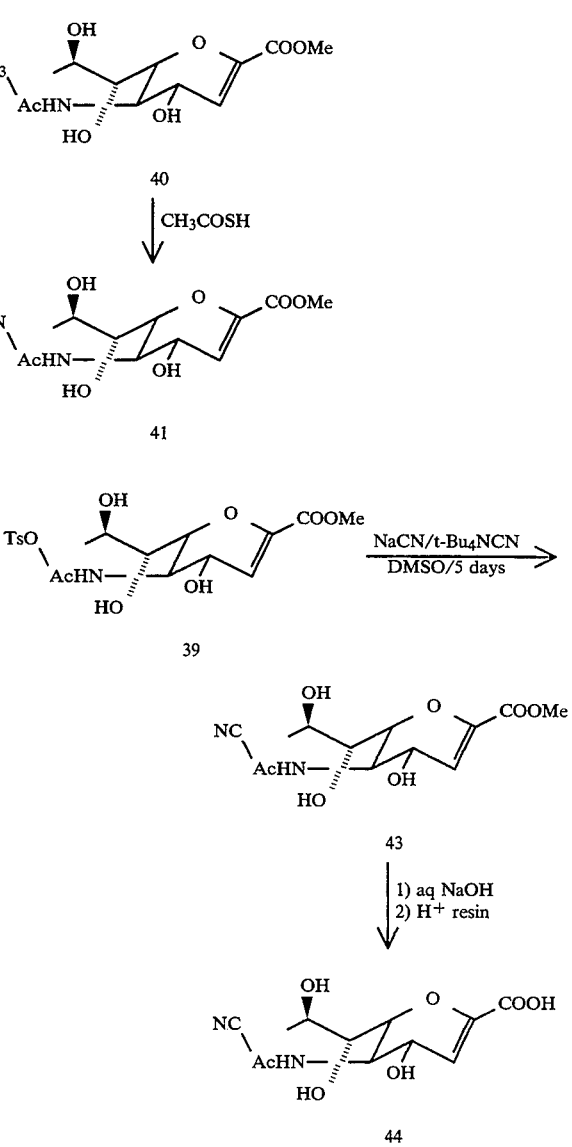

Methyl 5-acetamido-9-cyano-2,3,5,9-tetradeoxy-D-glycero-D-galacto-non-2-enopyranosonate (43) (80 mg., 0.25 mmol) was dissolved in 0.1M aq. sodium hydroxide (10 mL) and the resultant solution stirred at room temperature for 3 h.

The pH was then adjusted to 4 with Dowex 50W-X8 (H+), the resin filtered off and the filtrate lyophilized to give 75 mg (98% yield) of compound (43) as a fluffy white powder.

i.r. (KBr): $v_{max}$ (cm$^{-1}$) 3370 (s,OH), 2254 (w, CN), 1656 (s, NHAc) MS (FAB): 301 (M+H+) 1H nmr (300 MHz, D$_2$O): $\delta$ (ppm)=1.98 (s, 3H, NHAc), 2.70 (dd, 1H, H$_{9'}$), 2.88 (dd, 1H, J$_{9,9'}$ 17.27, H$_9$), 3.48 (d, 1H, H$_6$), 3.97 (dd, 1H, J$_{5,6}$ 9.84, H$_5$), 4.09–4.24 (m, 2H, H$_7$ and H$_8$, J$_{8,9}$ 3.90,J$_{8,9'}$ 6.53), 4.41 (dd, 1H, J$_{4,5}$ 8.87, H$_4$), 5.80 (d, 1H, J$_{3,4}$ 2.42, H$_3$)

EXAMPLE 20

Inhibition of Influenza Virus Neuraminidase

An in vitro bioassay of the above-described compounds against N2 influenza virus neuraminidase was conducted, following Warner and O'Brien, Biochemistry, 1979 18 2783–2787. For comparison, with the same assay the K$_i$ for 2-deoxy-N-acety-D-α-neuraminic acid was determined to be $3 \times 10^{-4}$M.

Values for K$_i$ were measured via a spectrofluorometric technique which uses the fluorogenic substrate 4-methylumbelliferyl N-acetylneuraminic acid (MUN), as described by Meyers et al., Anal. Biochem. 1980 101 166–174. For both enzymes, the assay mixture contained test compound at several concentrations between 0 and 2 mM, and approximately 1 mU enzyme in buffer (32.5 mM MES, 4 mM CaCl$_2$, pH 6.5 for N2; 32.5 mM acetate, 4 mM CaCl$_2$, pH 5.5 for *V. cholerae* neuraminidase).

The reaction was started by the addition of MUN to final concentrations of 75 or 40 μM. After 5 minutes at 37° C., 2.4 ml 0.1M glycine-NaOH, pH 10.2 was added to 0.1 ml reaction mixture to terminate the reaction. Fluorescence was read at excitation 365 nm, emission 450 nm, and appropriate MUN blanks (containing no enzyme) were subtracted from readings. The K$_i$ was estimated by Dixon plots (1/fluorescence versus compound concentration). Results are summarized in Table 1, and unless otherwise stated, refer to inhibition of N2 neuraminidase.

TABLE 1

Inhibition of Influenza Virus Neuraminidase In Vitro

| Compound | Ki (M) |
| --- | --- |
| 2-deoxy-N-acetyl-α-D-neuraminic acid | $3 \times 10^{-4}$ |
| sodium 5-acetamido-4-azido-2,3,4,5-tetradeoxy-D-glycero-D-galacto-non-2-enopyranosonate (4) | $2 \times 10^{-6}$ |
| sodium 5-acetamido-4-amino-2,3,4,5-tetradeoxy-D-glycero-D-galacto-non-2-enopyranosonate (6) | $6 \times 10^{-8}$ |
|  | $1.9 \times 10^{-7}$ (N9 neuraminidase, pH 6.5) |
|  | $1 \times 10^{-8}$ (N2 virus, pH 7.5) |
| ammonium 5-acetamido-4-guanidino-2,3,4,5-tetradeoxy-D-glycero-D-galacto-non-2-enopyranosonate (7) | $1.7 \times 10^{-8}$ |
|  | $>5 \times 10^{-8}$ (N9 neuraminidase) |
|  | $4.5 \times 10^{-4}$ (*V. cholerae* neuraminidase; pH 5.8) |
|  | $>10^{-2}$ (sheep neuraminidase; pH 4.5) |
| sodium 5-acetamido-4-N,N-diallylamino-2,3,4,5-tetradeoxy-D-glycero-D-galacto-non-2-enopyranosonate (9) | $4 \times 10^{-6}$ |
| sodium 5-acetamido-4-N-diallylamino-2,3,4,5-tetradeoxy-D-glycero-D-galacto-non-2-enopyranosonate (11) | $2.5 \times 10^{-6}$ (N2 and N9 neuraminidase) |
| Methyl 5-acetamido-7,8,9-tri-O-acetyl-4-amino-2,3,4,5-tetradeoxy-D-glycero-D-talo-non-2-enopyranosonate (12) | approx. $3 \times 10^{-3}$ |
| Methyl 7,8,9-tri-O-acetyl-2,3,5-trideoxy-4',5'-dihydro-2'-methyl-oxazolo [5,4-d] D-glycero-D-talo-non-2-enopyranosonate (13) | $3 \times 10^{-5}$ |
| sodium 5-acetamido-4-amino-2,3,4,5-tetradeoxy-D-glycero-D-talo-non-2-enopyranosonate (14) | $1 \times 10^{-7}$ (N2 and N9 neuraminidase) |
| Sodium 5-acetamido-4-azido-2,3,4,5-tetradeoxy-D-glycero-D-talo-non-2-enopyranosonate (17) | $2.8 \times 10^{-5}$ |
| Sodium 5-acetamido-4-N-methylamino-2,3,4.5-tetradeoxy-D-glycero-D-galacto-non-2-enopyranosonate (20) | $1.15 \times 10^{-6}$ |
| Sodium 5-acetamido-4-N,N-dimethylamino-2,3,4,5-tetradeoxy-D-glycero-D-galacto-non-2-enopyranosonate (23) | $7 \times 10^{-7}$ |
| Methyl 5-acetamido-4-N-methoxycarbonylmethylamino-2,3,4,5-tetradeoxy-D-glycero-D-galacto-non-2-enopyranosonate (25) | $7 \times 10^{-6}$ |
| Sodium 5-acetamido-4-N-2'-hydroxyethylamino-2,3,4,5-tetradeoxy-D-glycero-D-galacto-non-2-enopyranosonate (29) | $1.6 \times 10^{-6}$ (N2 and N9 neuraminidase) |
| Sodium 2,-3-dideoxy-D-glycero-D-galacto-non-2-enopyranosonate (35) | $4.8 \times 10^{-4}$ |
| Sodium 4,5-Diamino-2,3,4,5-tetradeoxy-D-glycero-D-galacto-non-2-enopyranosonate (38) | $6.5 \times 10^{-7}$ |
| Methyl 5,9-diacetamido-2,3,5,9-tetradeoxy-D-glycero-D-galacto-non-2-enopyranosonate (41) | $3.6 \times 10^{-5}$ |
| 5,9-diacetamido-2,3,5,9-tetradeoxy-D-glycero-D-galacto-non-2-enopyranosonic acid (42) | $1.45 \times 10^{-5}$ |
| Methyl 5-acetamido-9-cyano-2,3,5,9-tetradeoxy-D-glycero-D-galacto-non-2-enopyranosonate (43) | approx. $3 \times 10^{-3}$ |
| 5-Acetamido-9-cyano-2,3,5,9-tetradeoxy-D-glycero-D-galacto-non-2-enopyranosonic acid (44) | $3 \times 10^{-6}$ |

EXAMPLE 21

Inhibition of Influenza Virus Replication In Vitro

Inhibition of influenza A/Singapore/1/57 (H2 N2) and Influenza B/Victoria/102/85 replication in vitro was measured by reduction of viral plaque formation in Madin Darby canine kidney (MDCK) cells Monolayers of confluent MDCK cells, grown in six well tissue culture plates, were inoculated with 0.3 ml of virus diluted to give about 50–100 plaques/well. Virus was diluted in serum-free minimal essential medium (MEM) containing 2 µg/ml N-tosyl-l-phenylalanine chloromethyl ketone (TPCK) treated trypsin (Worthington Enzymes), and test compound.

Virus was adsorbed at room temperature for one hour, and the cells then overlaid with defined cell culture medium, version 1 (DCCM-1)/agar overlay containing test compound, 4 ml/well. DCCM-1 is a serum-free complete cell growth medium (Biological Industries), to which TPCK treated trypsin and DEAE-dextran to a final concentration of 2 µg/ml and 0.001% respectively, were added. Agar (5%) (Indubiose) was diluted 1:10 in the overlay before being added to the plate.

Once overlaid, plates were incubated at 37° C., 5% $CO_2$ for 3 days. Cells were then fixed with 5% glutaraldehyde, stained with carbol fuschin and the viral plaques counted. Results were as follows:

TABLE 2

| Compound | $IC_{50}$ Plaque Reduction (µM) | |
|---|---|---|
| | Influenza A | Influenza B |
| Sodium 5-Acetamido-4-amino-2,3,4,5-tetradeoxy-D-glycero-D-galacto-non-2-enopyranosonate (4-amino-Neu5Ac2en) (6) | 1.6 | 1.6 |
| Sodium 5-Acetamido-4-amino-2,3,4,5-tetra deoxy-D-glycero-D-talo-non-2-enopyranosonate (14). | 3.0 | 1.2 |
| Ammonium 5-Acetamido-4-guanidino-2,3,4,5-tetradeoxy-d-glycero-D-galacto-non-2-enopyranosonate (7) | 1.6 | 1.6 |
| Sodium 5-acetamido-4-N-2'-hydroxyethylamino-2,3,4,5-tetradeoxy-D-glycero-D-galacto-non-2-enopyranosonate (29) | 60 | 7 |
| Sodium 5-acetamido-4-N-allyl-N-hydroxy-2,3,4,5-tetradeoxy-D-glycero-D-galacto-non-2-enopyranosonate (45) | 4.7 | 2.7 |
| Sodium 4,5-Diamino-2,3,4,5-tetradeoxy-D-glycero-D-galacto-non-2-enopyranosonate (38) | 11 | 6.8 |

Sodium 5-acetamido-4-N-allyl-N-hydroxy-2,3,4,5-tetradeoxy-D-glycero-D-galacto-non-2-enopyranosonate (45) can readily be prepared from compound (11) described in Example 5, using oxidation methods.

EXAMPLE 22

In Vivo Anti-Viral Activity

The compounds of Examples 2,3 and 6 (4-amino, 4 guanidino and 4-epi-amino), as well as the compound DANA (2-deoxy-N-acetyl-D-α-neuraminic acid), which was shown in Example 20 to have anti-neuraminidase activity in vitro, were tested for anti-viral activity in a standard in vivo assay. When administered intranasally to mice before and during challenge with influenza A virus, these compounds reduced the titre of virus in lung tissue 1 to 3 days after infection.

Mice were infected intranasally with 50 µl of $10^3$ $TCID_{50}$ units/mouse of H2 N2 influenza A virus (A/Sing/1/57). The test compound was admionistered intranasally at a dose rate of either 12.5 or 25 mg/kg body weight (50 µl of aqueous solution/mouse) as follows: 24 hours and 3 hours before infection; 3 hours after infection then twice daily on each of days 1, 2 and 3 after infection. The structurally unrelated compounds ribavirin and amantadine were also used for comparison.

The mice were sacrificed on days 1, 2 and 3 after infection, their lungs removed and virus titres in the lungs measured. The titres were plotted graphically and expressed as the percentage area under the curves (AUC) compared to those for untreated mice. Results are summarized below.

TABLE 3

| Efficacy in Influenza Virus Infected Mice | | | |
|---|---|---|---|
| Experiment Number | Compound | Dose (mg/kg body weight) | % AUC |
| 1 | Sodium 5-Acetamido-4-amino-2,3,4,5-tetradeoxy-D-glycero-D-galacto-non-2-enopyranosonate (4-amino-Neu5Ac2en) (6) | 25 | 0.06 |
| | Amantadine | 25 | 0.08 |
| | DANA | 25 | 0.18 |
| 2 | Ammonium 5-Acetamido-4-guanidino-2,3,4,5-tetradeoxy-D-glycero-D-galacto-non-2-enopyranosonate (7) | 12.5 | 0.03 |
| | Ribavirin | 25 | 29.8 |
| | Amantadine | 25 | 0.2 |
| | | 12.5 | 0.03 |
| | DANA | 12.5 | 2.0 |
| 3 | Sodium 5-Acetamido-4-guanidino-2,3,4,5-tetradeoxy-D-glycero-D-galacto-non-2-enopyranosonate (14) | 12.5 | 21.1 |
| | Amantadine | 12.5 | 8.8 |
| | DANA | 12.5 | 48.0 |

All three compounds tested showed greater potency than DANA.

EXAMPLE 23

The following formulations are representative of compositions according to the invention:

|  | % w/w |
|---|---|
| AQUEOUS SOLUTION | |
| Compound of formula (I) | 10.0 |
| Benzalkonium chloride | 0.04 |
| Phenylethyl alcohol | 0.40 |
| Purified water | to 100% w/w |
| AQUEOUS COSOLVENT SOLUTION | |
| Compound of formula (I) | 10.0 |
| Benzalkonium chloride | 0.04 |
| Polyethylene glycol 400 | 10.0 |
| Propylene glycol | 30.0 |
| Purified water | to 100% w/w |
| AEROSOL FORMULATION | |
| Compound of formula (I) | 7.5 |
| Lecithin | 0.4 |
| Propellant 11 | 25.6 |
| Propellant 12 | 66.5 |
| DRY POWDER FORMULATION | |
| Compound of formula (I) | 40.0 |
| Lactose | 60.0 |

These formulations are prepared by admixture of the active ingredient and excipients by conventional pharmaceutical methods.

It will be clearly understood that the invention in its general aspect is not limited to the specific details referred to hereinabove.

We claim:

1. A compound of formula (Ib)

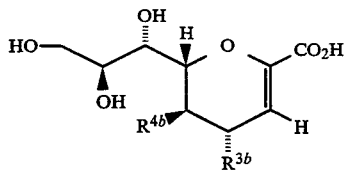

wherein $R^{3b}$ is $(alk)_x NR^{6b} R^{7b}$, CN or $N_3$;

where alk is an unsubstituted or substituted methylene;

x is 0 or 1;

$R^{6b}$ is hydrogen, $C_{1-6}$alkyl, aryl, aralkyl, amidine, $NR^{7b} R^{8b}$ or an unsaturated or saturated ring containing one or more heteroatoms selected from the group consisting of nitrogen, oxygen and sulphur;

$R^{7b}$ is hydrogen, $C_{1-6}$alkyl, or allyl;

$R^{8b}$ is hydrogen or $C_{1-6}$alkyl; and $R^{4b}$ is $NNHCOR^{9b}$ where $R^{9b}$ is hydrogen, substituted or unsubstituted $C_{1-4}$alkyl or aryl;

or a pharmaceutically acceptable salt or derivative thereof.

2. A compound as claimed in claim 1 wherein $R^{3b}$ is $NH_2$ or $NHC(=NH)NH_2$.

3. 5-acetamido-4-amino-2,3,4,5-tetradeoxy-D-glycero-D-galacto-non-2-enopyranosonic acid and pharmaceutically acceptable salts and derivatives thereof.

4. Sodium 5-acetamido-4-amino-2,3,4,5-tetradeoxy-D-glycero-D-galacto-non-2-enopyranosonate.

5. 5-acetamido-4-guanidino-2,3,4,5-tetradeoxy-D-glycero-D-galacto-non-2-enopyranosonic acid and pharmaceutically acceptable salts and derivatives thereof.

6. Ammonium 5-acetamido-4-guanidino-2,3,4,5-tetradeoxy-D-glycero-D-galacto-non-2-enopyranosonate.

7. A pharmaceutical formulation comprising a compound as claimed in claim 1 as active ingredient together with a pharmaceutically acceptable carrier therefor.

8. A pharmaceutical formulation suitable for intranasal administration comprising a compound as claimed in claim 1 as active ingredient together with a pharmaceutically acceptable carrier therefor.

9. A pharmaceutical formulation as claimed in claim 7 wherein the active ingredient is 5-acetamido-4-amino-2,3,4,5-tetradeoxy-D-glycero-D-galacto-non-2-enopyranosonic acid or a pharmaceutically acceptable salt thereof.

10. A pharmaceutical formulation as claimed in claim 7 wherein the active ingredient is 5-acetamido-4-guanidino-2,3,4,5-tetradeoxy-D-glycero-D-galacto-non-2-enopyranosonic acid or a pharmaceutically acceptable salt thereof.

* * * * *

UNITED STATES PATENT AND TRADEMARK OFFICE
CERTIFICATE OF CORRECTION

PATENT : 5,360,817
DATED : November 1, 1994
INVENTOR(S) : VON ITzSTEIN

It is certified that error appears in the above-identified patent and that said Letters Patent is hereby corrected as shown below:

Claim 1, column 38, line 9, delete "$NNHCOR^{9b}$" and insert --$NHCOR^{9b}$--.

Signed and Sealed this

Thirteenth Day of February, 2001

Attest:

NICHOLAS P. GODICI

*Attesting Officer*   *Acting Director of the United States Patent and Trademark Office*

UNITED STATES PATENT AND TRADEMARK OFFICE
CERTIFICATE OF CORRECTION

PATENT : 5,360,817
DATED : November 1, 1994
INVENTOR(S) : VON ITZSTEIN et al

It is certified that error appears in the above-identified patent and that said Letters Patent is hereby corrected as shown below:

(See Attachments For The Following Reactions)

Column 13-14, lines 1-25, delete the reaction as published and insert corrected reaction #1.

Column 15, lines 27-52, delete the reaction as published and insert corrected reaction #2.

Column 21-22, lines 37-54, delete the reaction as published and insert corrected reaction #3.

Column 23-34, lines 6-23, delete the reaction as published and insert corrected reacton #4.

Column 23-24, lines 29-45, delete the reaction as published and insert corrected reaction #5.

Column 25-26, lines 18-35, delete the reaction as published and insert corrected reaction #6.

Column 25-26, lines 42-59, delete the reaction as published and insert corrected reaction #7.

Column 27-28, lines 41-65, delete the reaction as published and insert corrected reaction #8.

Column 29-30, lines 6-26, delete the reaction as published and insert corrected reaction #9.

Column 31-32, lines 20-39, delete the reaction as published and insert corrected reaction #10.

Column 32, lines 40-46, delete the reaction as published and insert corrected reaction #11.

UNITED STATES PATENT AND TRADEMARK OFFICE
CERTIFICATE OF CORRECTION

PATENT NO. : 5,360,817
DATED : November 1, 1994
INVENTOR(S) : VON ITZSTEIN et al.

It is certified that error appears in the above-identified patent and that said Letters Patent is hereby corrected as shown below:

Claim 1, column 37, lines 37-45, please delete the formula (Ib), and insert:

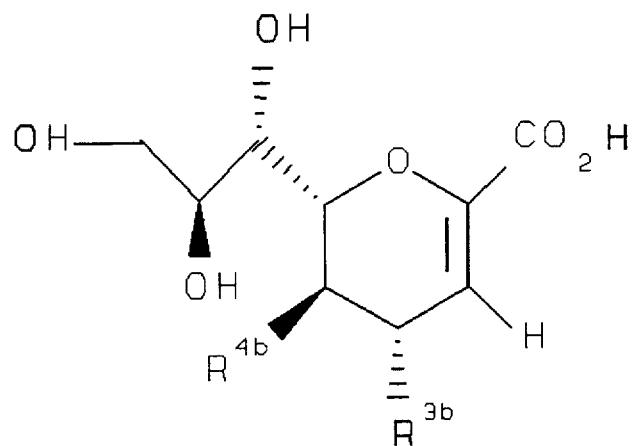

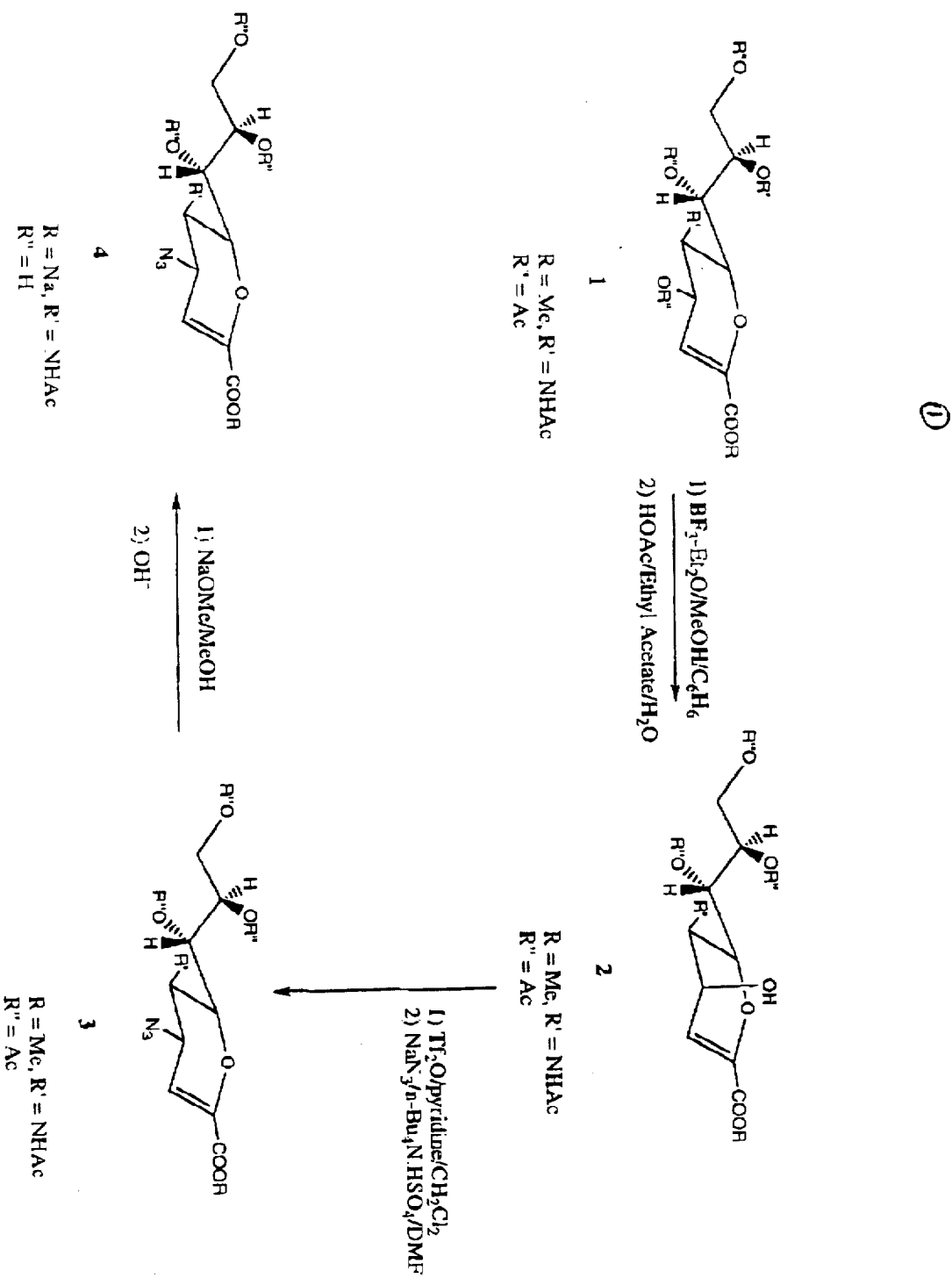

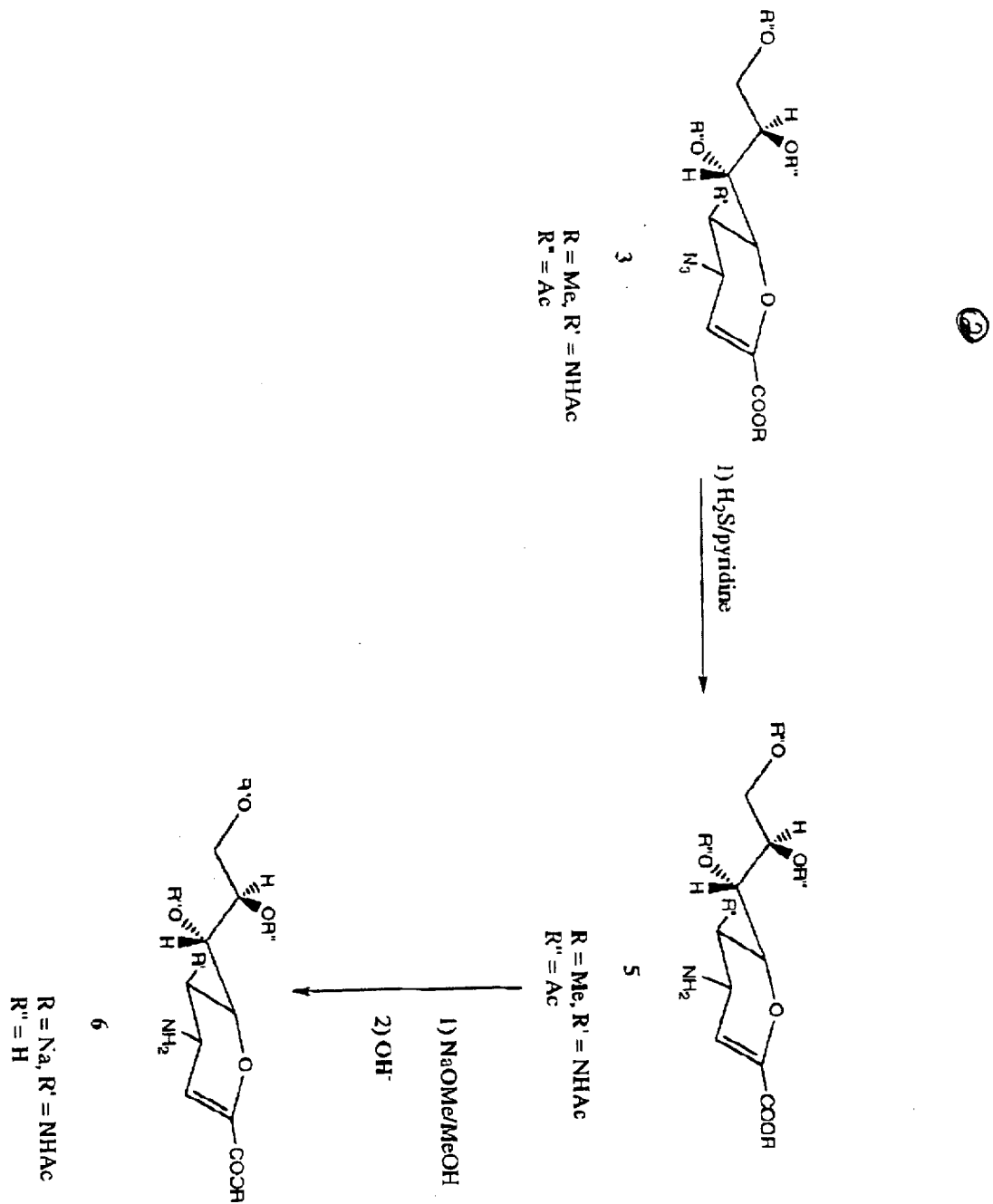

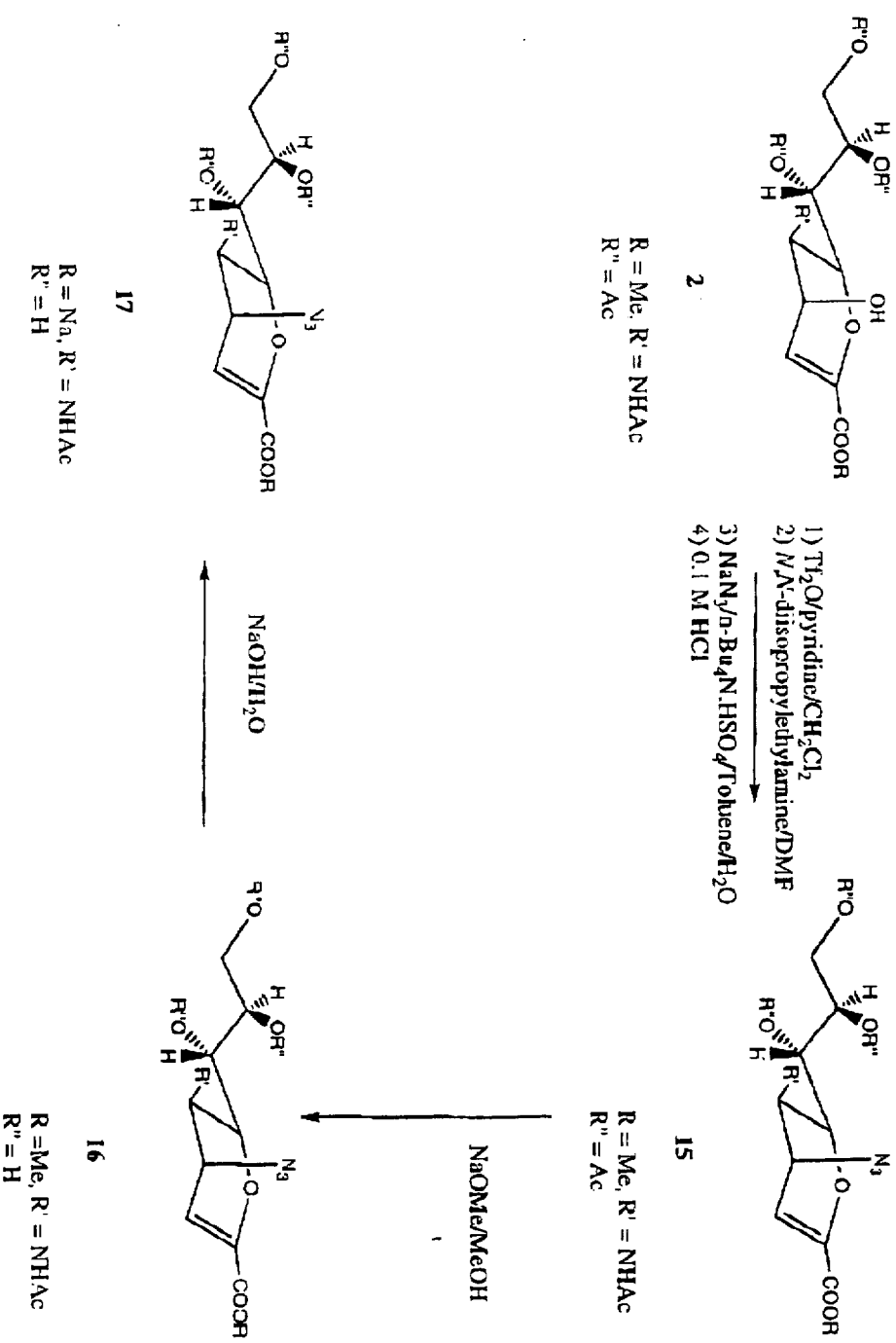

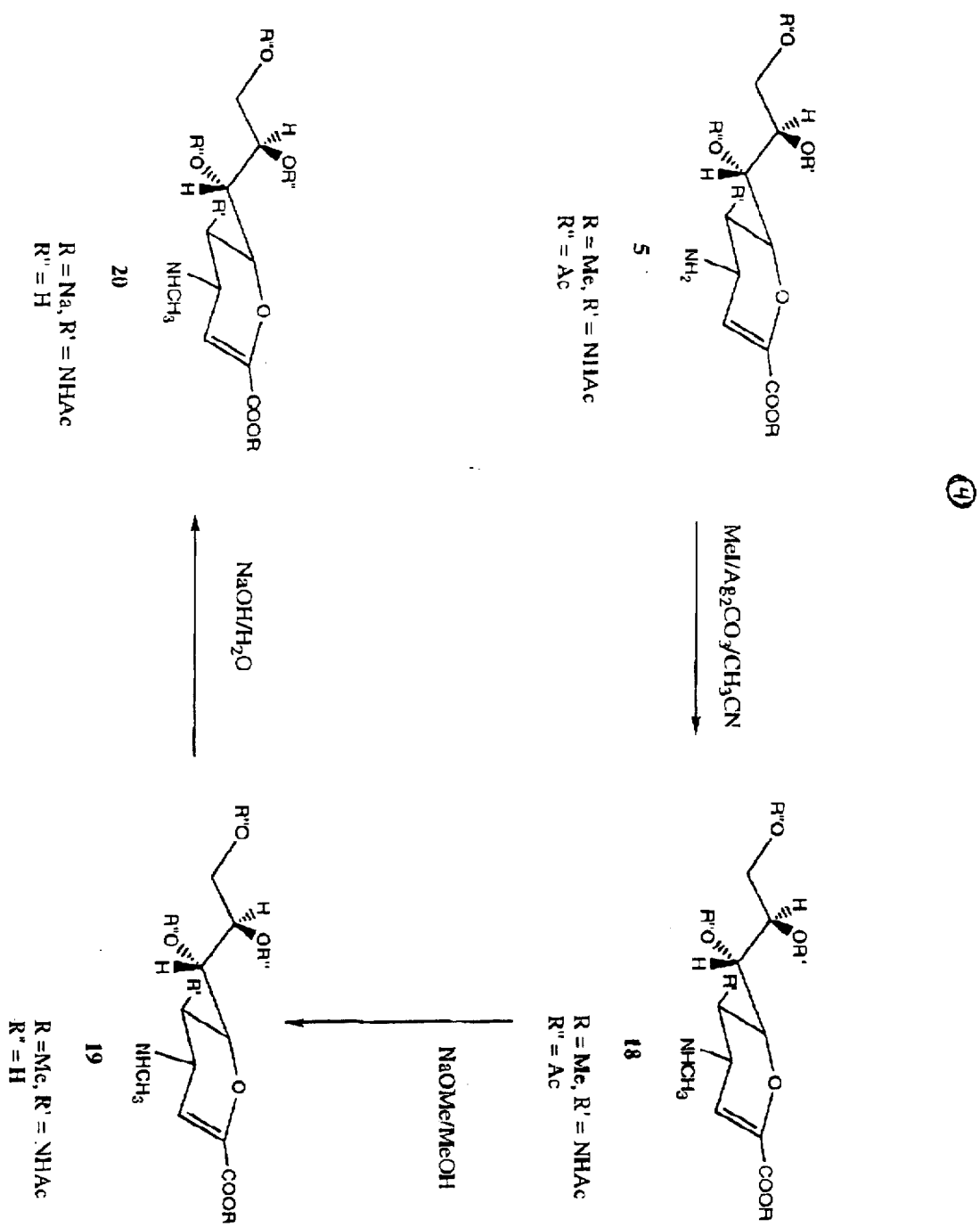

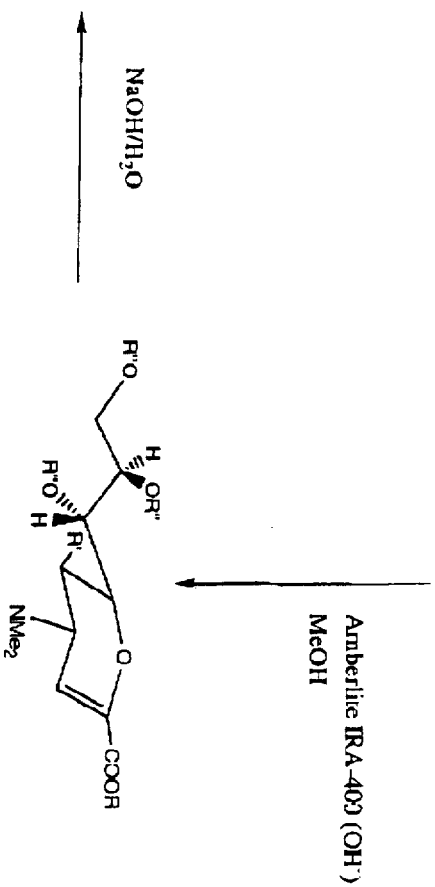

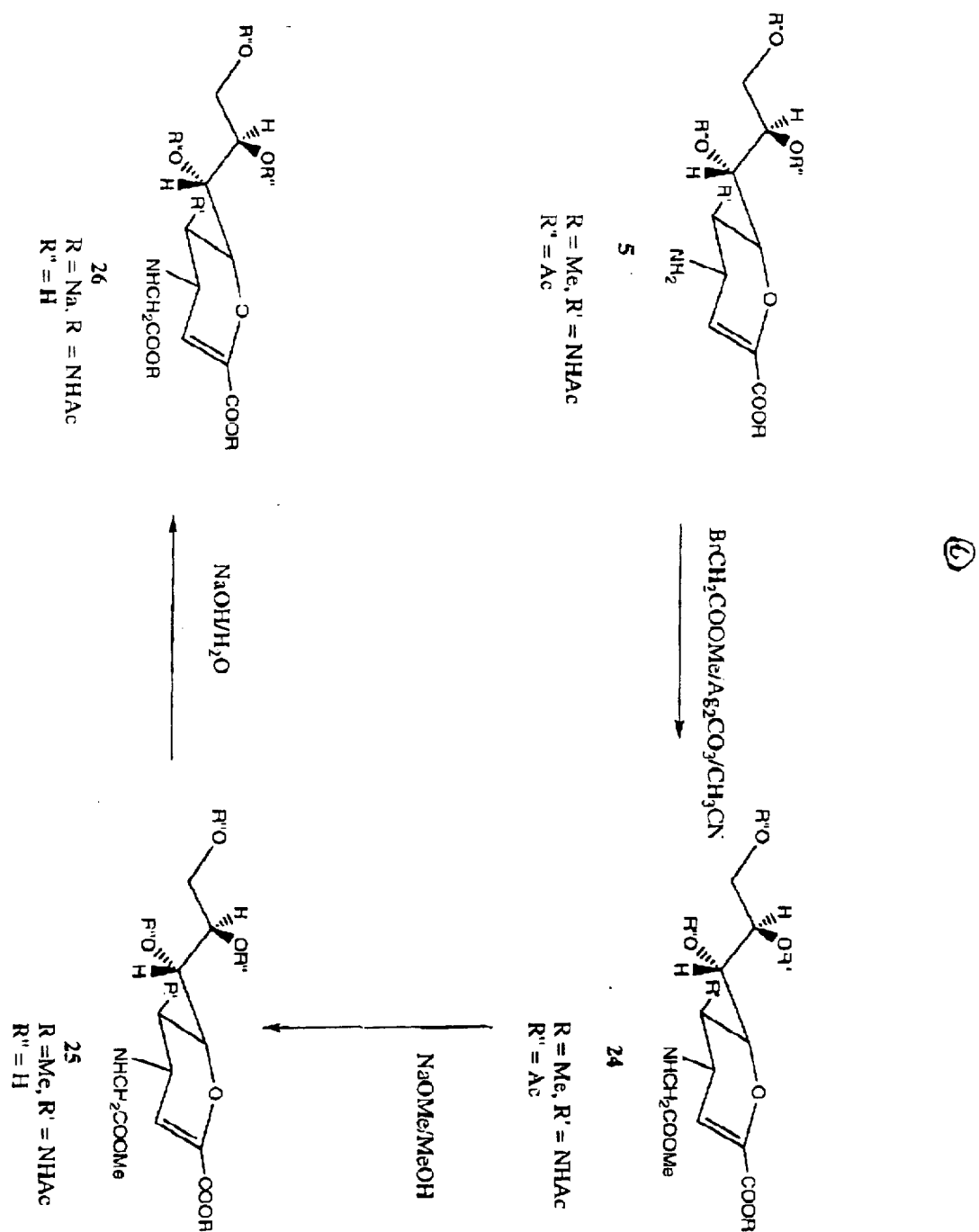

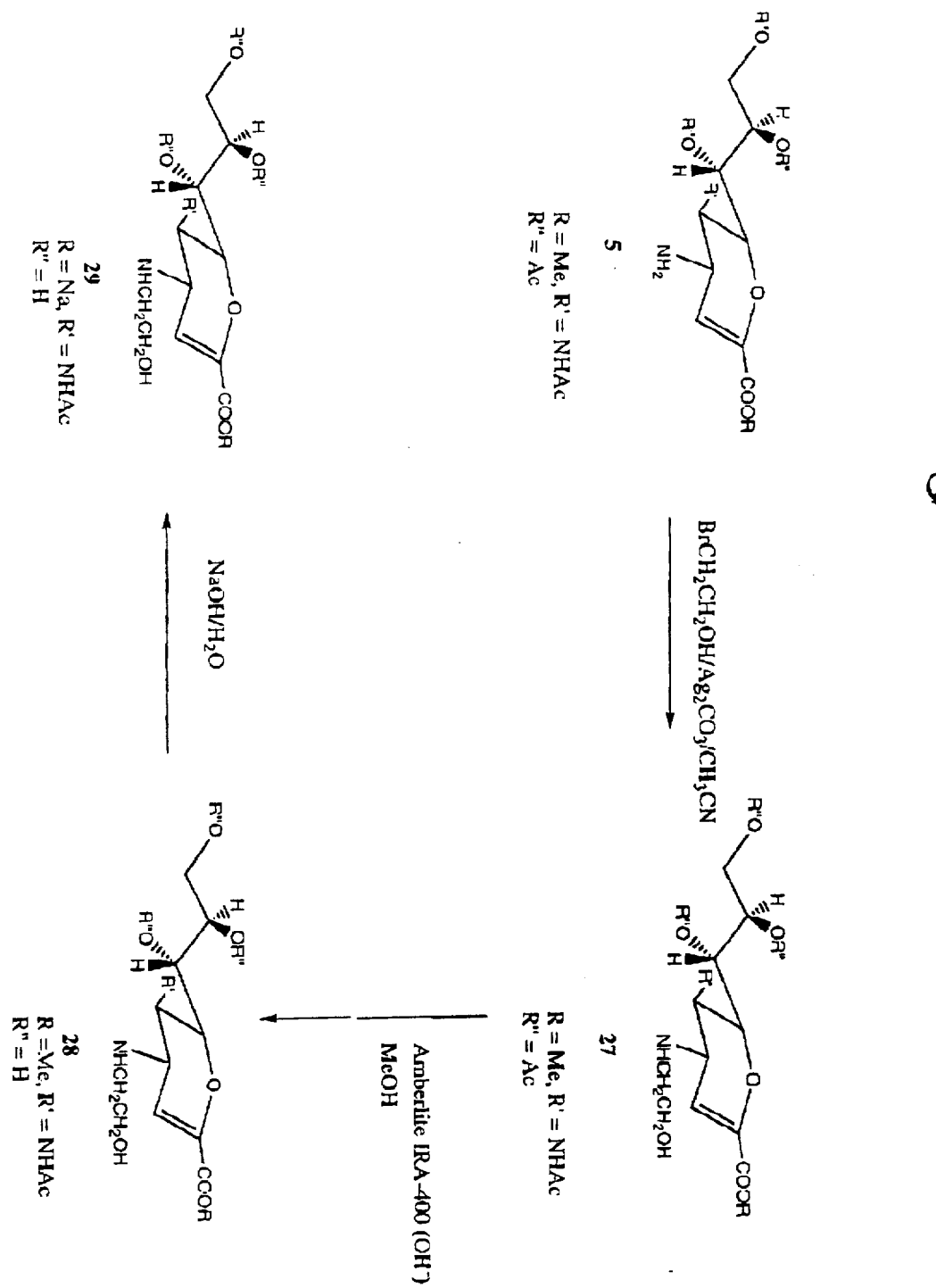

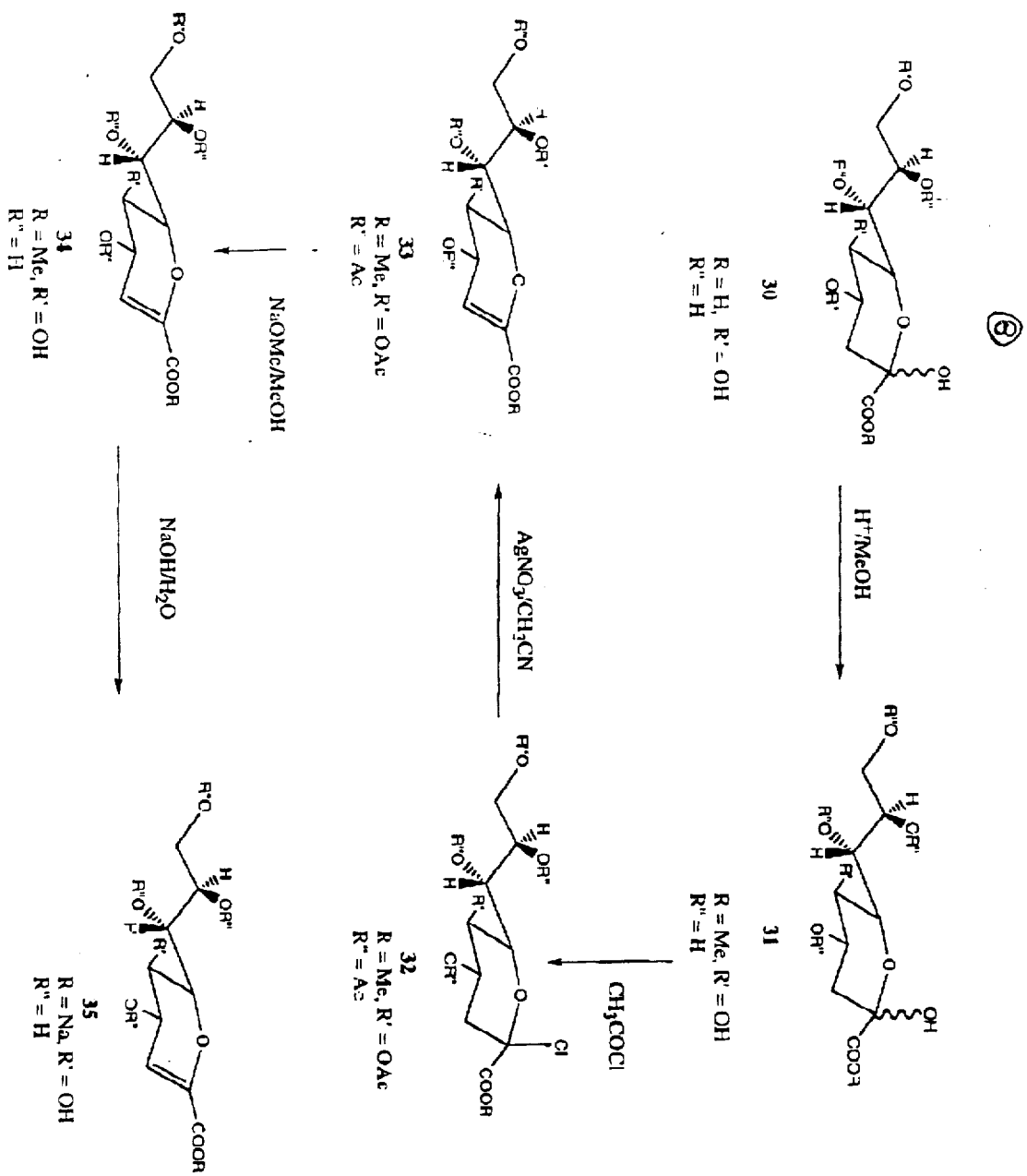

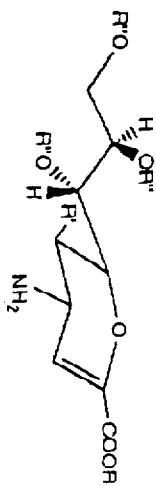
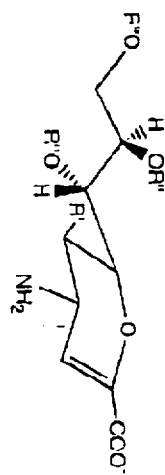
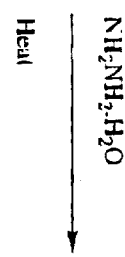
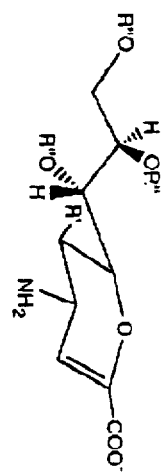

Pat. No. 5,360,817
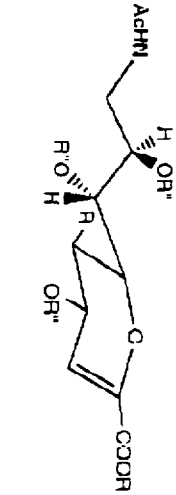
39
R = Me, R' = NHAc
R" = H
1) LiN₃/DMF/80°C
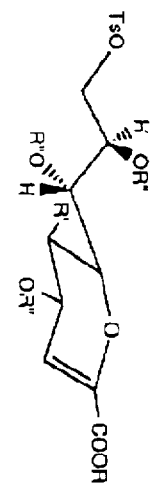
40
R = Me, R' = NHAc
R" = H
CH₃COSH
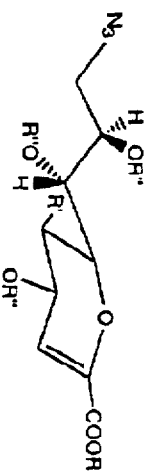
41
R = Me, R' = NHAc
R" = H
1) OH⁻
2) H⁺
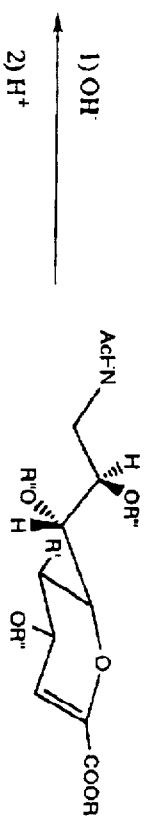
42
R = H, R' = NHAc
R" = H

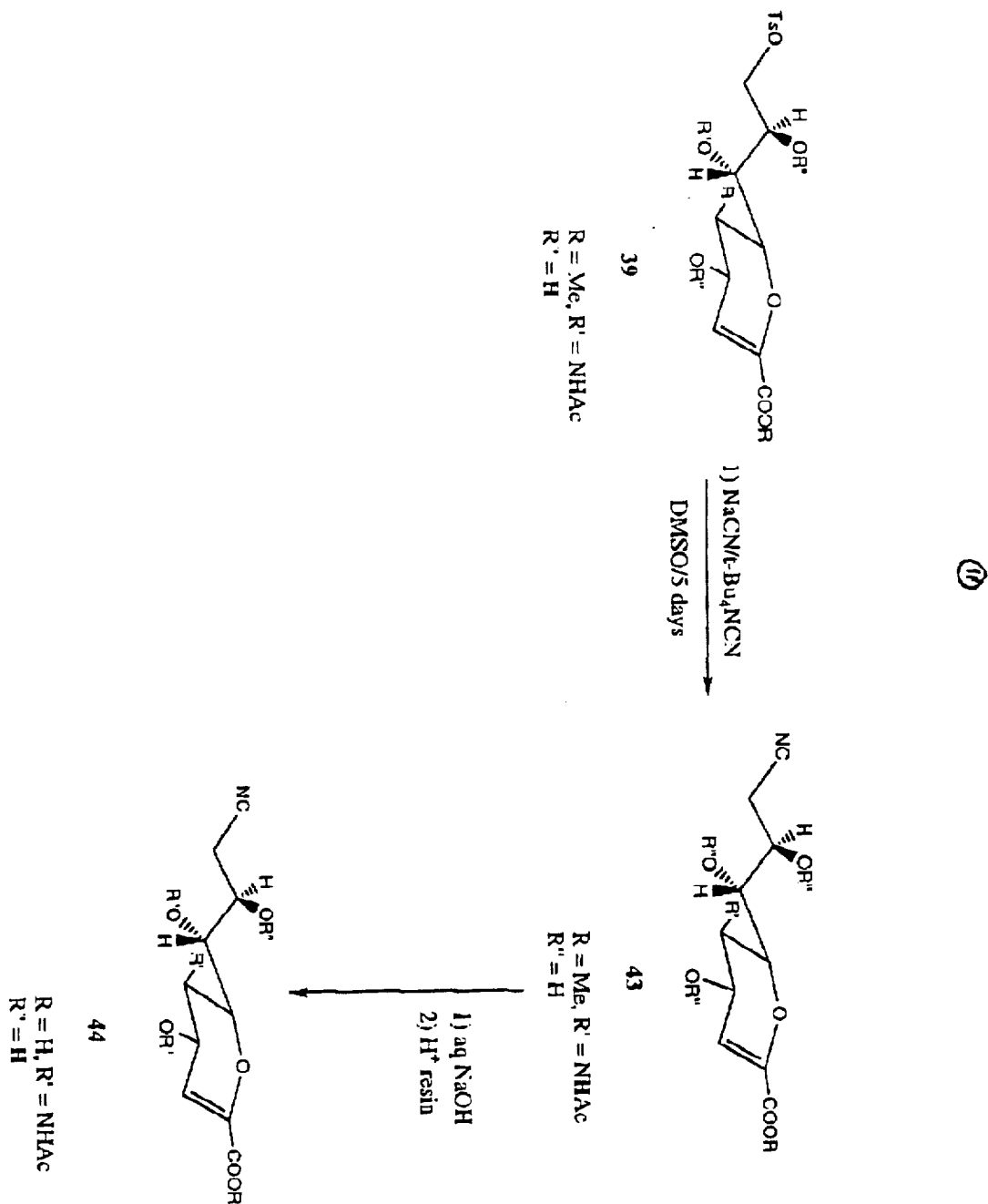

UNITED STATES PATENT AND TRADEMARK OFFICE

(12)          CERTIFICATE EXTENDING PATENT TERM
UNDER 35 U.S.C. § 156

| | | | |
|---|---|---|---|
| (68) | PATENT NO. | : | 5,360,817 |
| (45) | ISSUED | : | November 1, 1994 |
| (75) | INVENTOR | : | Von Izstein, et al. |
| (73) | PATENT OWNER | : | Biota Scientific Management Pty Ltd. |
| (95) | PRODUCT | : | RELENZA® (zanamivir) |

This is to certify that an application under 35 U.S.C. § 156 has been filed in the United States Patent and Trademark Office, requesting extension of the term of U.S. Patent No. 5,360,817 based upon the regulatory review of the product RELENZA® (zanamivir) by the Food and Drug Administration. Since it appears that the requirements of the law have been met, this certificate extends the term of the patent for the period of

(94)                  633 days from November 1, 2011, the original expiration date of the patent, subject to the payment of maintenance fees as provided by law, with all rights pertaining thereto as provided by 35 U.S.C. § 156(b).

I have caused the seal of the United States Patent and Trademark Office to be affixed this 7th day of January 2004.

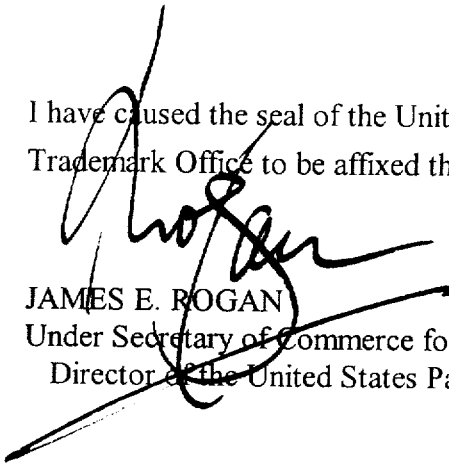

JAMES E. ROGAN
Under Secretary of Commerce for Intellectual Property and
Director of the United States Patent and Trademark Office

UNITED STATES PATENT AND TRADEMARK OFFICE
CERTIFICATE OF CORRECTION

| | | |
|---|---|---|
| PATENT NO. | : 5,360,817 | Page 1 of 1 |
| APPLICATION NO. | : 07/946327 | |
| DATED | : November 1, 1994 | |
| INVENTOR(S) | : Von Itzstein et al. | |

It is certified that error appears in the above-identified patent and that said Letters Patent is hereby corrected as shown below:

ON THE TITLE ITEM (75) AND (19) PLEASE DELETE VON IZSTEIN AND INSERT VON ITZSTEIN

Signed and Sealed this

Seventh Day of August, 2007

JON W. DUDAS
*Director of the United States Patent and Trademark Office*